(12) United States Patent
Rabiner et al.

(10) Patent No.: US 9,125,706 B2
(45) Date of Patent: Sep. 8, 2015

(54) DEVICES AND METHODS FOR BONE ALIGNMENT, STABILIZATION AND DISTRACTION

(71) Applicant: IlluminOss Medical, Inc., East Providence, RI (US)

(72) Inventors: Robert A. Rabiner, Tiverton, RI (US); Anthony W. O'Leary, Walpole, MA (US); Narissa Y. Chang, Mansfield, MA (US); Arnold-Peter C. Weiss, Barrington, RI (US); Lionel C. Bainbridge, Duffield/Belper (GB)

(73) Assignee: IlluminOss Medical, Inc., East Providence, RI (US)

( * ) Notice: Subject to any disclaimer, the term of this patent is extended or adjusted under 35 U.S.C. 154(b) by 0 days.

(21) Appl. No.: 14/551,650

(22) Filed: Nov. 24, 2014

(65) Prior Publication Data

US 2015/0080900 A1   Mar. 19, 2015

Related U.S. Application Data

(63) Continuation of application No. 13/617,181, filed on Sep. 14, 2012, now Pat. No. 8,915,966, which is a (Continued)

(51) Int. Cl.
*A61B 17/70* (2006.01)
*A61B 17/88* (2006.01)
(Continued)

(52) U.S. Cl.
CPC .............. *A61B 17/8811* (2013.01); *A61B 17/56* (2013.01); *A61B 17/8095* (2013.01);
(Continued)

(58) Field of Classification Search
CPC .............. A61F 2002/2835; A61F 2002/30579; A61F 2002/30904; A61F 2002/3055; A61F 2002/30581; A61F 2002/30841; A61F 2002/30556; A61F 2002/30583; A61F 2002/30538; A61F 2210/0085; A61F 2002/30616; A61B 17/025; A61B 2017/0256; A61B 17/1757; A61B 2017/681; A61B 17/7064; A61B 2017/567; A61B 2017/00411; A61B 17/8685; A61B 2017/00557; A61B 17/7068; A61B 17/7097
See application file for complete search history.

(56) References Cited

U.S. PATENT DOCUMENTS 4,280,233 A    7/1981  Raab
(Continued)

FOREIGN PATENT DOCUMENTS

DE    40 28 466    3/1992
(Continued)

OTHER PUBLICATIONS

Jovanovic et al., "Fixion Nails for Humeral Fractures, Injury", Int. J. Care Injured, vol. 35, Issue 11, pp. 1140-1142, Nov. 2004.
(Continued)

*Primary Examiner* — David Isabella
*Assistant Examiner* — Ann Schillinger
(74) *Attorney, Agent, or Firm* — Greenberg Traurig, LLP; David J. Dykeman; Roman Fayerberg

(57) ABSTRACT

An embodiment of a bone stabilization and distraction system of the present disclosure includes a light-sensitive liquid; a light source for providing light energy; a light-conducting fiber for delivering the light energy from the light source to cure the light-sensitive liquid; a delivery catheter having a proximal end in communication with the light-conducting fiber and the light-sensitive liquid, an inner lumen for passage of the light-conducting fiber, and an inner void for passage of the light-sensitive liquid; and an expandable body removably engaging a distal end of the delivery catheter, wherein the expandable body has a closed end, a sealable open end, an inner cavity for passage of the light-sensitive liquid, an external surface and an internal surface, and wherein the expandable body has an insertion depth with a fixed dimension, a width with a fixed dimension, and a thickness with a changeable dimension.

9 Claims, 13 Drawing Sheets

Related U.S. Application Data continuation of application No. 12/859,680, filed on Aug. 19, 2010, now Pat. No. 8,870,965.

(60) Provisional application No. 61/235,231, filed on Aug. 19, 2009.

(51) Int. Cl.

| | | |
|---|---|---|
| *A61B 17/56* | (2006.01) | |
| *A61B 17/80* | (2006.01) | |
| *A61B 17/00* | (2006.01) | |
| *A61F 2/30* | (2006.01) | |
| *A61F 2/46* | (2006.01) | |
| *A61N 5/06* | (2006.01) | |

(52) U.S. Cl.
CPC ......... *A61B17/8833* (2013.01); *A61B 17/7097* (2013.01); *A61B 2017/00411* (2013.01); *A61B 2017/883* (2013.01); *A61F 2002/30583* (2013.01); *A61F 2002/4696* (2013.01); *A61F 2210/0085* (2013.01); *A61N 5/0601* (2013.01); *A61N 5/062* (2013.01)

(56) References Cited

U.S. PATENT DOCUMENTS

| | | |
|---|---|---|
| 4,294,251 A | 10/1981 | Greenwald et al. |
| 4,313,434 A | 2/1982 | Segal |
| 4,341,691 A | 7/1982 | Anuta |
| 4,369,772 A | 1/1983 | Miller |
| 4,414,608 A | 11/1983 | Furihata |
| 4,422,719 A | 12/1983 | Orcutt |
| 4,433,898 A | 2/1984 | Nasiri |
| 4,462,394 A | 7/1984 | Jacobs |
| 4,466,435 A | 8/1984 | Murray |
| 4,562,598 A | 1/1986 | Kranz |
| 4,686,973 A | 8/1987 | Frisch |
| 4,697,584 A | 10/1987 | Haynes |
| 4,735,625 A | 4/1988 | Davidson |
| 4,870,953 A | 10/1989 | DonMicheal et al. |
| 4,888,024 A | 12/1989 | Powlan |
| 4,892,550 A | 1/1990 | Huebsch |
| 4,904,391 A | 2/1990 | Freeman |
| 4,961,424 A | 10/1990 | Kubota et al. |
| 4,963,151 A | 10/1990 | Ducheyne et al. |
| 4,969,888 A | 11/1990 | Scholten et al. |
| 5,030,093 A | 7/1991 | Mitnick |
| 5,049,157 A | 9/1991 | Mittelmeier et al. |
| 5,085,660 A | 2/1992 | Lin |
| 5,092,899 A | 3/1992 | Forte |
| 5,102,413 A | 4/1992 | Poddar |
| 5,108,404 A | 4/1992 | Scholten et al. |
| 5,112,333 A | 5/1992 | Fixel |
| 5,207,669 A | 5/1993 | Baker et al. |
| 5,295,733 A | 3/1994 | LeBegue |
| 5,295,962 A | 3/1994 | Crocker et al. |
| 5,303,718 A | 4/1994 | Krajicek |
| 5,316,550 A | 5/1994 | Forte |
| 5,336,699 A | 8/1994 | Cooke et al. |
| 5,372,598 A | 12/1994 | Luhr et al. |
| 5,376,123 A | 12/1994 | Klaue et al. |
| 5,391,144 A | 2/1995 | Sakurai et al. |
| 5,415,654 A | 5/1995 | Daikuzono |
| 5,423,850 A | 6/1995 | Berger |
| 5,432,876 A | 7/1995 | Appeldorn et al. |
| 5,443,468 A | 8/1995 | Johnson |
| 5,462,552 A | 10/1995 | Kiester |
| 5,480,400 A | 1/1996 | Berger |
| 5,538,514 A | 7/1996 | Hawkins |
| 5,548,676 A | 8/1996 | Savage, Jr. |
| 5,554,111 A | 9/1996 | Morrey et al. |
| 5,556,429 A | 9/1996 | Felt |
| 5,571,204 A | 11/1996 | Nies |
| 5,658,310 A | 8/1997 | Berger |
| 5,658,963 A | 8/1997 | Qian et al. |
| 5,705,181 A | 1/1998 | Cooper et al. |
| 5,707,374 A | 1/1998 | Schmidt |
| 5,713,901 A | 2/1998 | Tock |
| 5,795,353 A | 8/1998 | Felt |
| 5,824,087 A | 10/1998 | Aspden et al. |
| 5,827,289 A | 10/1998 | Reiley et al. |
| 5,888,220 A | 3/1999 | Felt et al. |
| 5,897,557 A | 4/1999 | Chin et al. |
| 5,908,433 A | 6/1999 | Eager et al. |
| 5,972,015 A | 10/1999 | Scribner et al. |
| 5,980,075 A | 11/1999 | Sheaffer |
| 5,980,253 A | 11/1999 | Oxman et al. |
| 5,987,199 A | 11/1999 | Zarian et al. |
| 5,989,230 A | 11/1999 | Frassica |
| 5,997,570 A | 12/1999 | Ligtenberg et al. |
| 6,008,264 A | 12/1999 | Ostler |
| 6,019,761 A | 2/2000 | Gustilo |
| 6,019,774 A | 2/2000 | Weiss et al. |
| 6,033,411 A | 3/2000 | Preissman |
| 6,039,762 A | 3/2000 | McKay |
| 6,042,380 A | 3/2000 | De Rowe |
| 6,048,346 A | 4/2000 | Reiley et al. |
| 6,053,917 A | 4/2000 | Sherman et al. |
| 6,059,789 A | 5/2000 | Dinger et al. |
| 6,066,154 A | 5/2000 | Reiley et al. |
| 6,077,265 A | 6/2000 | Werding et al. |
| 6,079,868 A | 6/2000 | Rydell |
| 6,103,203 A | 8/2000 | Fischer |
| 6,110,176 A | 8/2000 | Shapira |
| 6,121,341 A | 9/2000 | Sawhney et al. |
| 6,127,597 A | 10/2000 | Beyar et al. |
| 6,136,011 A | 10/2000 | Stambaugh |
| 6,140,452 A | 10/2000 | Felt et al. |
| 6,159,236 A | 12/2000 | Biel |
| 6,179,852 B1 | 1/2001 | Strickland et al. |
| 6,195,477 B1 | 2/2001 | Denuto et al. |
| 6,200,134 B1 | 3/2001 | Kovac et al. |
| 6,217,581 B1 | 4/2001 | Tolson |
| 6,223,085 B1 | 4/2001 | Dann et al. |
| 6,224,630 B1 | 5/2001 | Bao et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,258,089 B1 | 7/2001 | Campbell et al. |
| 6,261,289 B1 | 7/2001 | Levy |
| 6,280,456 B1 | 8/2001 | Scribner et al. |
| 6,282,013 B1 | 8/2001 | Ostler et al. |
| 6,290,382 B1 | 9/2001 | Bourn et al. |
| 6,299,597 B1 | 10/2001 | Buscemi et al. |
| 6,306,177 B1 | 10/2001 | Felt et al. |
| 6,319,255 B1 | 11/2001 | Grundei et al. |
| 6,332,894 B1 | 12/2001 | Stalcup et al. |
| 6,336,914 B1 | 1/2002 | Gillespie, III |
| 6,336,930 B1 | 1/2002 | Stalcup et al. |
| 6,358,252 B1 | 3/2002 | Shapira |
| 6,387,098 B1 | 5/2002 | Cole et al. |
| 6,395,007 B1 | 5/2002 | Bhatnagar et al. |
| 6,416,531 B2 | 7/2002 | Chen |
| 6,416,737 B1 | 7/2002 | Manolagas et al. |
| 6,419,483 B1 | 7/2002 | Adam et al. |
| 6,423,055 B1 | 7/2002 | Farr et al. |
| 6,423,083 B2 | 7/2002 | Reiley et al. |
| 6,425,923 B1 | 7/2002 | Stalcup et al. |
| 6,440,444 B2 | 8/2002 | Boyce et al. |
| 6,443,988 B2 | 9/2002 | Felt et al. |
| 6,447,514 B1 | 9/2002 | Stalcup et al. |
| 6,458,375 B1 | 10/2002 | Gertzman et al. |
| 6,478,751 B1 | 11/2002 | Krueger et al. |
| 6,482,234 B1 | 11/2002 | Weber et al. |
| 6,485,512 B1 | 11/2002 | Cheng |
| 6,494,883 B1 | 12/2002 | Ferree |
| 6,524,251 B2 | 2/2003 | Rabiner et al. |
| 6,524,313 B1 | 2/2003 | Fassier et al. |
| 6,551,321 B1 | 4/2003 | Burkinshaw et al. |
| 6,551,337 B1 | 4/2003 | Rabiner et al. |
| 6,565,528 B1 | 5/2003 | Mueller |
| 6,579,277 B1 | 6/2003 | Rabiner et al. |

(56) References Cited

U.S. PATENT DOCUMENTS

| | | |
|---|---|---|
| 6,579,279 B1 | 6/2003 | Rabiner et al. |
| 6,620,185 B1 | 9/2003 | Harvie et al. |
| 6,623,505 B2 | 9/2003 | Scribner et al. |
| 6,632,235 B2 | 10/2003 | Weikel et al. |
| 6,648,881 B2 | 11/2003 | KenKnight et al. |
| 6,652,547 B2 | 11/2003 | Rabiner et al. |
| 6,652,587 B2 | 11/2003 | Felt et al. |
| 6,660,013 B2 | 12/2003 | Rabiner et al. |
| 6,679,873 B2 | 1/2004 | Rabiner et al. |
| 6,695,781 B2 | 2/2004 | Rabiner et al. |
| 6,695,782 B2 | 2/2004 | Rabiner et al. |
| 6,696,073 B2 | 2/2004 | Boyce et al. |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,730,048 B1 | 5/2004 | Hare et al. |
| 6,733,451 B2 | 5/2004 | Rabiner et al. |
| 6,733,513 B2 | 5/2004 | Boyle et al. |
| 6,740,093 B2 | 5/2004 | Hochschuler et al. |
| 6,755,862 B2 | 6/2004 | Keynan |
| 6,783,530 B1 | 8/2004 | Levy |
| 6,802,835 B2 | 10/2004 | Rabiner et al. |
| 6,818,018 B1 | 11/2004 | Sawhney |
| 6,852,095 B1 | 2/2005 | Ray |
| 6,866,678 B2 | 3/2005 | Shenderova et al. |
| 6,869,442 B2 | 3/2005 | Cheng |
| 6,875,212 B2 | 4/2005 | Shaolian et al. |
| 6,885,246 B2 | 4/2005 | Tsutsui et al. |
| 6,887,246 B2 | 5/2005 | Bhatnagar et al. |
| 6,887,275 B2 | 5/2005 | Carchidi et al. |
| 6,899,713 B2 | 5/2005 | Shaolian et al. |
| 6,899,719 B2 | 5/2005 | Reiley et al. |
| 6,932,843 B2 | 8/2005 | Smith et al. |
| 6,964,667 B2 | 11/2005 | Shaolian et al. |
| 6,979,341 B2 | 12/2005 | Scribner et al. |
| 6,981,981 B2 | 1/2006 | Reiley et al. |
| 7,001,431 B2 | 2/2006 | Bao et al. |
| 7,008,433 B2 | 3/2006 | Voellmicke et al. |
| 7,048,731 B2 | 5/2006 | Altshuler et al. |
| 7,052,498 B2 | 5/2006 | Levy et al. |
| 7,077,865 B2 | 7/2006 | Bao et al. |
| 7,124,067 B2 | 10/2006 | Ascenzi |
| 7,141,061 B2 | 11/2006 | Williams et al. |
| 7,144,414 B2 | 12/2006 | Harvie et al. |
| 7,153,305 B2 | 12/2006 | Johnson et al. |
| 7,156,861 B2 | 1/2007 | Scribner et al. |
| 7,156,880 B2 | 1/2007 | Evans et al. |
| 7,169,140 B1 | 1/2007 | Kume |
| 7,215,863 B1 | 5/2007 | Arenella et al. |
| 7,241,303 B2 | 7/2007 | Reiss et al. |
| 7,252,677 B2 | 8/2007 | Burwell et al. |
| 7,258,692 B2 | 8/2007 | Thelen et al. |
| 7,261,720 B2 | 8/2007 | Stevens et al. |
| 7,320,709 B2 | 1/2008 | Felt et al. |
| 7,341,601 B2 | 3/2008 | Eisermann et al. |
| 7,360,542 B2 | 4/2008 | Nelson et al. |
| 7,407,616 B2 | 8/2008 | Melikechi et al. |
| 7,419,450 B2 | 9/2008 | Ito |
| 7,427,295 B2 | 9/2008 | Ellman et al. |
| 7,465,318 B2 | 12/2008 | Sennett et al. |
| 7,547,319 B2 | 6/2009 | Segal et al. |
| 7,628,800 B2 | 12/2009 | Sherman et al. |
| 7,632,277 B2 | 12/2009 | Woll et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,740,656 B2 | 6/2010 | Mensah et al. |
| 7,744,555 B2 | 6/2010 | DiMauro et al. |
| 7,766,965 B2 | 8/2010 | Bao et al. |
| 7,771,476 B2 | 8/2010 | Justis et al. |
| 7,776,075 B2 | 8/2010 | Bruneau et al. |
| 7,806,900 B2 | 10/2010 | Rabiner |
| 7,811,284 B2 | 10/2010 | Rabiner |
| 7,811,286 B2 | 10/2010 | Medoff |
| 7,811,290 B2 | 10/2010 | Rabiner |
| 7,842,040 B2 | 11/2010 | Rabiner et al. |
| 7,850,711 B1 | 12/2010 | Stone et al. |
| 7,857,748 B2 | 12/2010 | Williams et al. |
| 7,879,041 B2 | 2/2011 | Rabiner et al. |
| 7,912,539 B2 | 3/2011 | Doty et al. |
| 7,947,015 B2 | 5/2011 | Herweck et al. |
| 8,034,071 B2 | 10/2011 | Scribner et al. |
| 8,123,807 B2 | 2/2012 | Kim |
| 8,210,729 B2 | 7/2012 | O'Leary et al. |
| 8,211,121 B1 | 7/2012 | Quinn et al. |
| 8,246,628 B2 | 8/2012 | Rabiner |
| 8,328,402 B2 | 12/2012 | O'Leary et al. |
| 8,348,956 B2 | 1/2013 | Rabiner |
| 8,366,711 B2 | 2/2013 | Rabiner et al. |
| 8,403,968 B2 | 3/2013 | Rabiner et al. |
| 8,413,664 B2 | 4/2013 | Appling |
| 8,512,338 B2 | 8/2013 | Rabiner et al. |
| 8,574,233 B2 | 11/2013 | Rabiner et al. |
| 8,668,701 B2 | 3/2014 | Rabiner et al. |
| 8,672,982 B2 | 3/2014 | Rabiner et al. |
| 8,684,965 B2 | 4/2014 | Rabiner et al. |
| 8,708,955 B2 | 4/2014 | Tilson et al. |
| 8,734,460 B2 | 5/2014 | Rabiner et al. |
| 8,764,761 B2 | 7/2014 | Truckai et al. |
| 8,870,965 B2 | 10/2014 | Rabiner et al. |
| 8,906,030 B2 | 12/2014 | Rabiner et al. |
| 8,906,031 B2 | 12/2014 | Rabiner et al. |
| 8,915,966 B2 | 12/2014 | Rabiner et al. |
| 8,936,382 B2 | 1/2015 | O'Leary et al. |
| 8,936,644 B2 | 1/2015 | Rabiner et al. |
| 8,939,977 B2 | 1/2015 | DiPoto et al. |
| 9,005,254 B2 | 4/2015 | Rabiner et al. |
| 2001/0011174 A1 | 8/2001 | Reiley et al. |
| 2001/0044626 A1 | 11/2001 | Reiley et al. |
| 2002/0082600 A1 | 6/2002 | Shaolian et al. |
| 2002/0156482 A1 | 10/2002 | Scribner et al. |
| 2002/0161373 A1 | 10/2002 | Osorio et al. |
| 2002/0198526 A1 | 12/2002 | Shaolian et al. |
| 2003/0028210 A1 | 2/2003 | Boyle et al. |
| 2003/0083642 A1 | 5/2003 | Boyd et al. |
| 2003/0105469 A1 | 6/2003 | Karmon |
| 2003/0114914 A1 | 6/2003 | Cheng |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. |
| 2004/0006341 A1 | 1/2004 | Shaolian et al. |
| 2004/0024388 A1 | 2/2004 | Altshuler |
| 2004/0034434 A1 | 2/2004 | Evans et al. |
| 2004/0059333 A1 | 3/2004 | Carl et al. |
| 2004/0059417 A1 | 3/2004 | Smith et al. |
| 2004/0092948 A1 | 5/2004 | Stevens et al. |
| 2004/0098015 A1 | 5/2004 | Weikel et al. |
| 2004/0117025 A1 | 6/2004 | Reindel |
| 2004/0133280 A1 | 7/2004 | Trieu |
| 2004/0167561 A1 | 8/2004 | Boucher et al. |
| 2004/0167625 A1 | 8/2004 | Beyar et al. |
| 2004/0225296 A1 | 11/2004 | Reiss et al. |
| 2004/0228142 A1 | 11/2004 | Takada et al. |
| 2004/0230309 A1 | 11/2004 | Di Mauro et al. |
| 2004/0247641 A1 | 12/2004 | Felt et al. |
| 2005/0010231 A1 | 1/2005 | Myers |
| 2005/0015140 A1 | 1/2005 | deBeer |
| 2005/0015148 A1 | 1/2005 | Jansen et al. |
| 2005/0018989 A1 | 1/2005 | Shimizu et al. |
| 2005/0043733 A1 | 2/2005 | Eisermann et al. |
| 2005/0043808 A1 | 2/2005 | Felt et al. |
| 2005/0049691 A1 | 3/2005 | Mericle et al. |
| 2005/0090901 A1 | 4/2005 | Studer |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0228260 A1 | 10/2005 | Burwell et al. |
| 2005/0234453 A1 | 10/2005 | Shaolian et al. |
| 2005/0251140 A1 | 11/2005 | Shaolian et al. |

(56) References Cited

U.S. PATENT DOCUMENTS

| | | | |
|---|---|---|---|
| 2005/0284485 A9 | 12/2005 | Nelson et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0084985 A1 | 4/2006 | Kim et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1 | 6/2006 | Truckai et al. |
| 2006/0142747 A1 | 6/2006 | Appling |
| 2006/0155296 A1 | 7/2006 | Richter |
| 2006/0173464 A1 | 8/2006 | Ellman et al. |
| 2006/0183811 A1 | 8/2006 | Melikechi et al. |
| 2006/0184246 A1 | 8/2006 | Zwirkoski |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0247787 A1 | 11/2006 | Rydell et al. |
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0100327 A1 | 5/2007 | Smith |
| 2007/0104416 A1 | 5/2007 | Shimizu et al. |
| 2007/0118143 A1 | 5/2007 | Ralph et al. |
| 2007/0123876 A1 | 5/2007 | Czartoski et al. |
| 2007/0123877 A1 | 5/2007 | Goldin et al. |
| 2007/0123878 A1 | 5/2007 | Shaver et al. |
| 2007/0161991 A1 | 7/2007 | Altarac et al. |
| 2007/0198023 A1 | 8/2007 | Sand et al. |
| 2007/0225705 A1 | 9/2007 | Osorio et al. |
| 2007/0233146 A1 | 10/2007 | Henniges et al. |
| 2007/0239148 A1 | 10/2007 | Scheller |
| 2007/0255287 A1 | 11/2007 | Rabiner |
| 2008/0015500 A1 | 1/2008 | Herweck et al. |
| 2008/0019657 A1 | 1/2008 | Maitland et al. |
| 2008/0021474 A1 | 1/2008 | Bonutti et al. |
| 2008/0039854 A1 | 2/2008 | Rabiner |
| 2008/0080205 A1 | 4/2008 | Forrester et al. |
| 2008/0103505 A1 | 5/2008 | Fransen |
| 2008/0125784 A1 | 5/2008 | Rabiner et al. |
| 2008/0154266 A1 | 6/2008 | Protopsaltis et al. |
| 2008/0154368 A1 | 6/2008 | Justis |
| 2008/0154373 A1 | 6/2008 | Protopsaltis et al. |
| 2008/0183122 A1 | 7/2008 | Fisher et al. |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburger et al. |
| 2009/0018524 A1 | 1/2009 | Greenhalgh et al. |
| 2009/0024166 A1 | 1/2009 | Carl et al. |
| 2009/0048629 A1 | 2/2009 | Rabiner |
| 2009/0054900 A1 | 2/2009 | Rabiner et al. |
| 2009/0093887 A1 | 4/2009 | Walter et al. |
| 2009/0112196 A1 | 4/2009 | Rabiner et al. |
| 2009/0118833 A1 | 5/2009 | Hudgins et al. |
| 2009/0171265 A1 | 7/2009 | Doty et al. |
| 2009/0171358 A1 | 7/2009 | Chang et al. |
| 2009/0177204 A1 | 7/2009 | Colleran et al. |
| 2009/0182336 A1 | 7/2009 | Brenzel et al. |
| 2009/0187192 A1 | 7/2009 | Rabiner et al. |
| 2009/0216232 A1 | 8/2009 | Buford, III et al. |
| 2009/0228007 A1 | 9/2009 | Justin et al. |
| 2009/0254064 A1 | 10/2009 | Boatman |
| 2009/0287309 A1 | 11/2009 | Walch et al. |
| 2009/0306589 A1 | 12/2009 | Tilson et al. |
| 2010/0234958 A1 | 9/2010 | Linares |
| 2010/0241178 A1 | 9/2010 | Tilson et al. |
| 2010/0249942 A1 | 9/2010 | Goswami et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0318087 A1 | 12/2010 | Scribner et al. |
| 2010/0331850 A1 | 12/2010 | Rabiner |
| 2011/0004213 A1 | 1/2011 | Rabiner et al. |
| 2011/0009871 A1 | 1/2011 | Rabiner |
| 2011/0029093 A1 | 2/2011 | Bojarski et al. |
| 2011/0046746 A1 | 2/2011 | Rabiner et al. |
| 2011/0082504 A1 | 4/2011 | Singhatt et al. |
| 2011/0098713 A1 | 4/2011 | Rabiner et al. |
| 2011/0110114 A1 | 5/2011 | Papac et al. |
| 2011/0112588 A1 | 5/2011 | Linderman et al. |
| 2011/0118740 A1 | 5/2011 | Rabiner et al. |
| 2011/0137317 A1 | 6/2011 | O'Halloran et al. |
| 2011/0160870 A1 | 6/2011 | Baumgartner et al. |
| 2011/0166306 A1 | 7/2011 | Stansbury et al. |
| 2011/0313356 A1 | 12/2011 | Rabiner et al. |
| 2012/0029102 A1 | 2/2012 | Rose et al. |
| 2012/0041557 A1 | 2/2012 | Frigg |
| 2012/0165941 A1 | 6/2012 | Rabiner et al. |
| 2012/0259375 A1 | 10/2012 | Druma et al. |
| 2012/0262939 A1 | 10/2012 | O'Leary et al. |
| 2012/0289968 A1 | 11/2012 | Rabiner |
| 2012/0316652 A1 | 12/2012 | Renganath et al. |
| 2013/0003406 A1 | 1/2013 | O'Leary et al. |
| 2013/0006304 A1 | 1/2013 | Rabiner et al. |
| 2013/0012998 A1 | 1/2013 | Altarac et al. |
| 2013/0013008 A1 | 1/2013 | Rabiner et al. |
| 2013/0013009 A1 | 1/2013 | Colleran et al. |
| 2013/0013010 A1 | 1/2013 | Rabiner et al. |
| 2013/0018482 A1 | 1/2013 | Meridew et al. |
| 2013/0023876 A1 | 1/2013 | Rabiner et al. |
| 2013/0023877 A1 | 1/2013 | Rabiner et al. |
| 2013/0023886 A1 | 1/2013 | Rabiner et al. |
| 2013/0041472 A1 | 2/2013 | Rabiner et al. |
| 2013/0046390 A1 | 2/2013 | Rabiner et al. |
| 2013/0066326 A1 | 3/2013 | Rabiner et al. |
| 2013/0158607 A1 | 6/2013 | Rabiner et al. |
| 2013/0184715 A1 | 7/2013 | Rabiner et al. |
| 2014/0018806 A1 | 1/2014 | DiPoto et al. |
| 2014/0135847 A1 | 5/2014 | Rabiner et al. |
| 2014/0142581 A1 | 5/2014 | Rabiner et al. |
| 2014/0148813 A1 | 5/2014 | Rabiner et al. |
| 2014/0163453 A1 | 6/2014 | Rabiner et al. |
| 2014/0180288 A1 | 6/2014 | Rabiner et al. |
| 2015/0066028 A1 | 3/2015 | Rabiner et al. |
| 2015/0066085 A1 | 3/2015 | Rabiner et al. |
| 2015/0080900 A1 | 3/2015 | Rabiner et al. |
| 2015/0088268 A1 | 3/2015 | Rabiner et al. |

FOREIGN PATENT DOCUMENTS

| | | |
|---|---|---|
| EP | 0 709 698 | 5/1996 |
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 98/38918 | 9/1998 |
| WO | WO 99/43266 | 9/1999 |
| WO | WO 02/43628 | 6/2002 |
| WO | WO 03/047472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | WO 2005/112804 | 12/2005 |
| WO | WO 2006/016807 | 2/2006 |
| WO | WO 2007/002251 | 1/2007 |

(56) References Cited

FOREIGN PATENT DOCUMENTS

| | | |
|---|---|---|
| WO | WO 2007/059259 | 5/2007 |
| WO | WO 2007/075375 | 7/2007 |
| WO | WO 2007/127255 | 11/2007 |
| WO | WO 2007/127260 | 11/2007 |
| WO | WO 2008/039811 | 4/2008 |
| WO | WO 2008/063265 | 5/2008 |
| WO | WO 2009/059090 | 5/2009 |
| WO | WO 2009/064847 | 5/2009 |
| WO | WO 2009/082688 | 7/2009 |
| WO | WO 2009/088927 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | WO 2011/071567 | 6/2011 |
| WO | WO 2011/162910 | 12/2011 |
| WO | WO 2012/051312 | 4/2012 |
| WO | WO 2012/088432 | 6/2012 |
| WO | WO 2013/013069 | 1/2013 |
| WO | WO 2013/013071 | 1/2013 |
| WO | WO 2013/013072 | 1/2013 |
| WO | WO 2013/059609 | 4/2013 |
| WO | WO 2014/011669 | 1/2014 |
| WO | WO 2014/100427 | 6/2014 |

OTHER PUBLICATIONS

Maruyama et al., "Metacarpal Fracture Fixation with Absorbable Polyglycolide Rods and Stainless Steel K Wires: A Biomechanical Comparison", Journal of Biomedical Materials Research (Applied Biomaterials), vol. 33, Issue 1, pp. 9-12, Apr. 1996.
Waris et al., "Bioabsorbable Miniplating Versus Metallic Fixation for Metacarpal Fractures", Clinical Orthopaedics and Related Research, No. 410, pp. 310-319, May 2003.
Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.
PCT International Search Report based on PCT/US07/20402 dated Apr. 1, 2008.
PCT International Search Report based on PCT/US07/10050 dated Apr. 17, 2008.
PCT International Search Report based on PCT/US07/10038 dated Aug. 27, 2008.
PCT International Search Report based on PCT/US08/81929 dated Jan. 12, 2009.
PCT International Search Report based on PCT/US08/81924 dated Feb. 9, 2009.
PCT International Search Report based on PCT/US08/87630 dated Feb. 24, 2009.
USPTO Office Action in U.S. Appl. No. 11/789,906 mailed Apr. 29, 2009.
USPTO Office Action in U.S. Appl. No. 11/789,906 mailed Mar. 11, 2010.
USPTO Office Action in U.S. Appl. No. 11/789,906 mailed Apr. 30, 2010.
USPTO Office Action in U.S. Appl. No. 11/789,907 mailed May 11, 2010.
USPTO Office Action in U.S. Appl. No. 11/903,123 mailed Jul. 1, 2010.
PCT International Search Report based on PCT/US10/30275 dated Aug. 11, 2010.
USPTO Office Action in U.S. Appl. No. 12/262,411 mailed Sep. 1, 2010.
USPTO Office Action in U.S. Appl. No. 11/964,370 mailed Dec. 9, 2010.
PCT International Search Report based on PCT/US10/56219 dated Jan. 20, 2011.
PCT International Search Report based on PCT/US10/46003 dated May 24, 2011.
PCT International Search Report based on PCT/US11/38389 dated Sep. 22, 2011.
USPTO Office Action in U.S. Appl. No. 11/964,370 mailed Apr. 28, 2011.
USPTO Office Action in U.S. Appl. No. 11/964,370 mailed Sep. 23, 2011.
USPTO Office Action in U.S. Appl. No. 12/858,924 mailed Oct. 24, 2011.
USPTO Office Action in U.S. Appl. No. 12/755,784 mailed Dec. 23, 2011.
USPTO Office Action in U.S. Appl. No. 12/886,288 mailed Dec. 27, 2011.
USPTO Office Action in U.S. Appl. No. 12/875,460 mailed Mar. 8, 2012.
USPTO Office Action in U.S. Appl. No. 11/964,370 mailed Mar. 16, 2012.
USPTO Office Action in U.S. Appl. No. 12/858,924 mailed Apr. 4, 2012.
PCT International Search Report based on PCT/US11/66871 dated May 1, 2012.
USPTO Office Action in U.S. Appl. No. 12/756,014 mailed May 11, 2012.
USPTO Office Action in U.S. Appl. No. 12/262,370 mailed May 29, 2012.
USPTO Office Action in U.S. Appl. No. 12/943,544 mailed Jun. 8, 2012.
USPTO Office Action in U.S. Appl. No. 12/886,288 mailed Jun. 26, 2012.
USPTO Office Action in U.S. Appl. No. 11/964,370 mailed Jul. 6, 2012.
Extended European Search Report based on EP 07 75 6022 dated Jul. 19, 2012.
Extended European Search Report based on EP 07 75 6016 dated Jul. 18, 2012.
USPTO Office Action in U.S. Appl. No. 12/755,784 mailed Aug. 1, 2012.
USPTO Office Action in U.S. Appl. No. 12/858,924 mailed Aug. 2, 2012.
USPTO Office Action in U.S. Appl. No. 12/886,288 mailed Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 mailed Oct. 25, 2012.
USPTO Office Action in U.S. Appl. No. 12/859,680 mailed Nov. 9, 2012.
USPTO Office Action in U.S. Appl. No. 12/943,544 mailed Dec. 3, 2012.
USPTO Office Action in U.S. Appl. No. 12/262,370 mailed Dec. 14, 2012.
International Search Report and Written Opinion for PCT/US2012/061047 mailed Jan. 7, 2013.
USPTO Office Action in U.S. Appl. No. 12/859,680 mailed Jan. 17, 2013.
USPTO Office Action in U.S. Appl. No. 12/756,014 mailed Jan. 22, 2013.
USPTO Office Action in U.S. Appl. No. 13/088,916 mailed Jan. 23, 2013.
USPTO Office Action in U.S. Appl. No. 13/617,557 mailed Feb. 4, 2013.
USPTO Office Action in U.S. Appl. No. 12/755,784 mailed Mar. 13, 2013.
USPTO Office Action in U.S. Appl. No. 13/616,416 mailed Mar. 25, 2013.
USPTO Office Action in U.S. Appl. No. 13/561,249 mailed Apr. 23, 2013.
USPTO Office Action in U.S. Appl. No. 12/262,370 mailed Apr. 26, 2013.

(56) References Cited

OTHER PUBLICATIONS

USPTO Office Action in U.S. Appl. No. 13/088,916 mailed May 13, 2013.
Supplemental European Search Report based on EP 08 87 7881 dated May 15, 2013.
USPTO Office Action in U.S. Appl. No. 13/772,947 mailed Jun. 19, 2013.
USPTO Office Action in U.S. Appl. No. 12/859,680 mailed Jul. 9, 2013.
USPTO Office Action in U.S. Appl. No. 13/561,249 mailed Sep. 16, 2013.
USPTO Office Action in U.S. Appl. No. 13/088,916 mailed Sep. 17, 2013.
USPTO Office Action in U.S. Appl. No. 12/943,544 mailed Sep. 25, 2013.
PCT International Search Report based on PCT/US13/049773 dated Oct. 1, 2013.
USPTO Office Action in U.S. Appl. No. 13/617,557 mailed Oct. 9, 2013.
Extended European Search Report based on EP 10 76 2390 dated Oct. 30, 2013.
USPTO Office Action in U.S. Appl. No. 12/262,370 mailed Nov. 21, 2013.
USPTO Office Action in U.S. Appl. No. 12/983,496 mailed Feb. 5, 2014.
USPTO Office Action in U.S. Appl. No. 12/756,014 mailed Feb. 13, 2014.
USPTO Office Action in U.S. Appl. No. 13/617,181 mailed Feb. 25, 2014.
PCT International Search Report based on PCT/US13/076598 dated Mar. 19, 2014.
USPTO Office Action in U.S. Appl. No. 13/655,808 mailed Mar. 27, 2014.
USPTO Office Action in U.S. Appl. No. 13/553,247 mailed May 7, 2014.
Extended European Search Report based on EP 14156473 dated May 13, 2014.
USPTO Office Action in U.S. Appl. No. 13/800,518 mailed Jun. 10, 2014.
USPTO Office Action in U.S. Appl. No. 12/262,370 mailed Jun. 26, 2014.
USPTO Office Action in U.S. Appl. No. 13/617,557 mailed Jun. 27, 2014.
USPTO Office Action in U.S. Appl. No. 13/335,110 mailed Jul. 31, 2014.
USPTO Office Action in U.S. Appl. No. 13/616,781 mailed Aug. 26, 2014.
USPTO Office Action in U.S. Appl. No. 13/730,521 mailed Sep. 8, 2014.
USPTO Office Action in U.S. Appl. No. 12/756,014 mailed Oct. 7, 2014.
USPTO Office Action in U.S. Appl. No. 13/553,450 mailed Oct. 24, 2014.
USPTO Office Action in U.S. Appl. No. 13/335,110 mailed Oct. 24, 2014.
USPTO Office Action in U.S. Appl. No. 13/553,247 mailed Dec. 5, 2014.
USPTO Office Action in U.S. Appl. No. 13/553,051 mailed Dec. 23, 2014.
USPTO Office Action in U.S. Appl. No. 12/262,370 mailed Jan. 14, 2015.
USPTO Office Action in U.S. Appl. No. 13/617,557 mailed Jan. 15, 2015.
USPTO Office Action in U.S. Appl. No. 13/335,110 mailed Feb. 9, 2015.
USPTO Office Action in U.S. Appl. No. 13/796,085 mailed Feb. 12, 2015.
USPTO Office Action in U.S. Appl. No. 13/553,051 mailed Mar. 31, 2015.

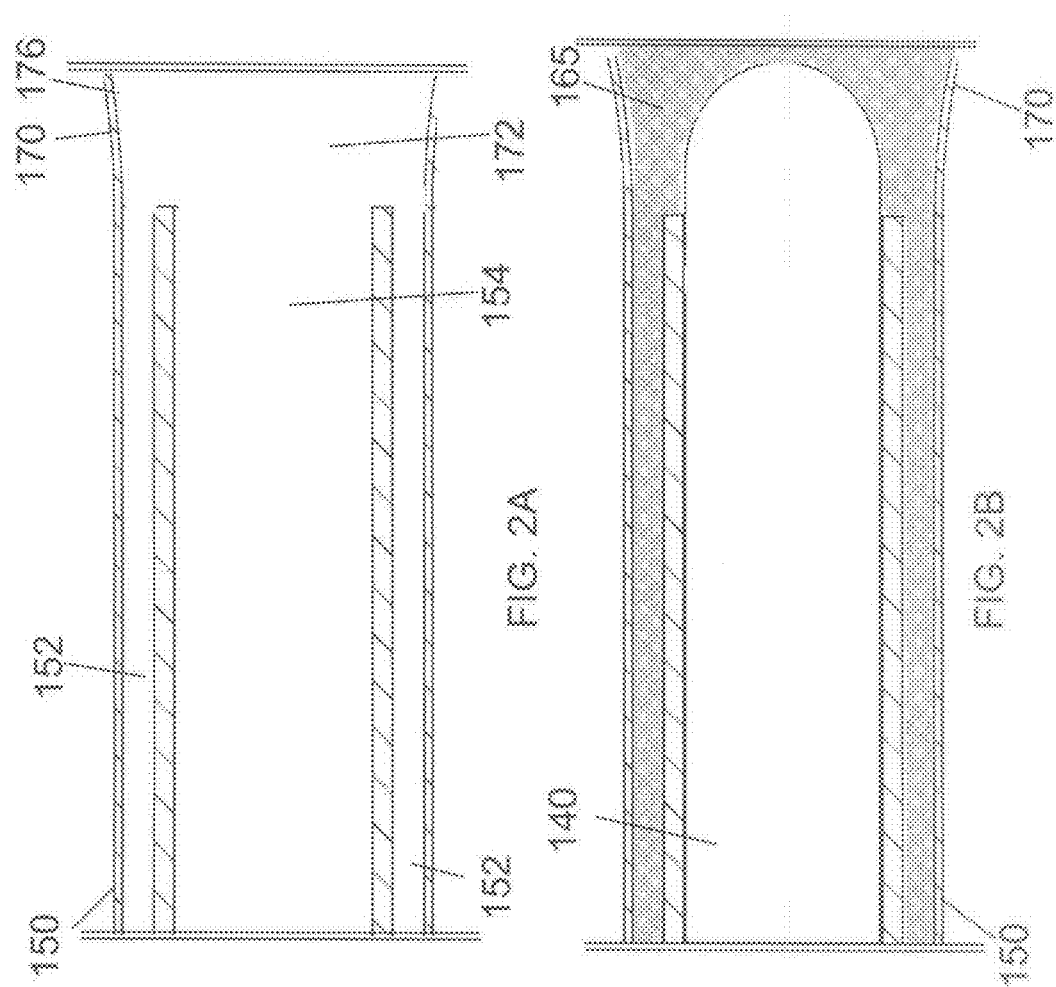

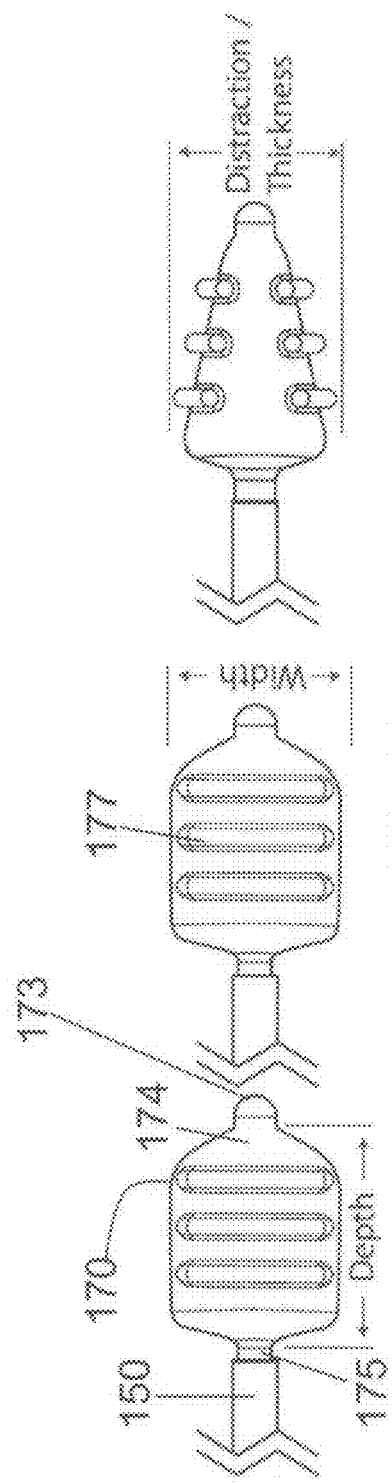
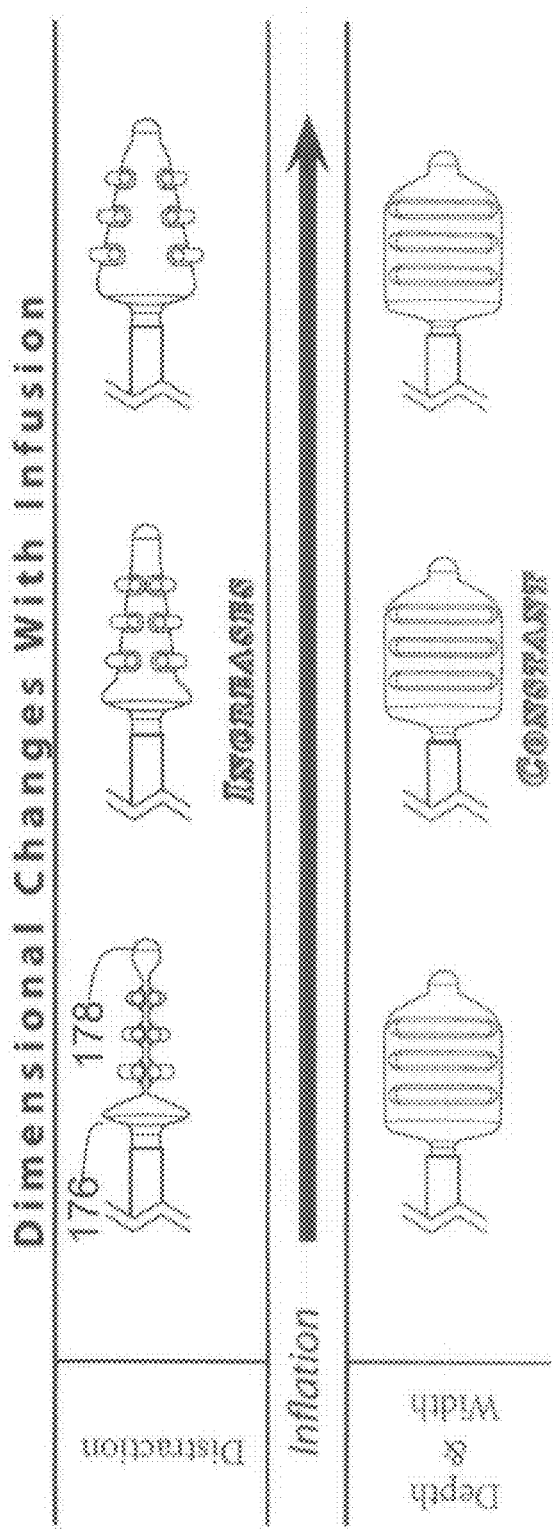
FIG. 4A
FIG. 4B

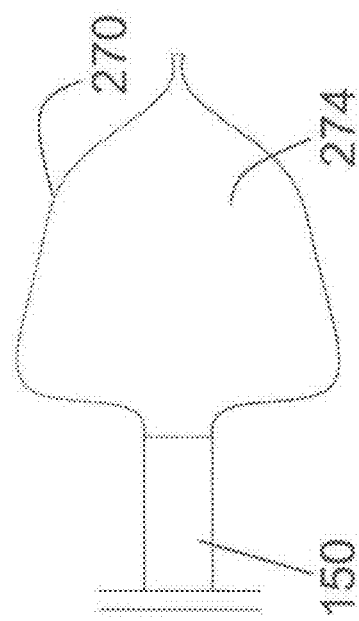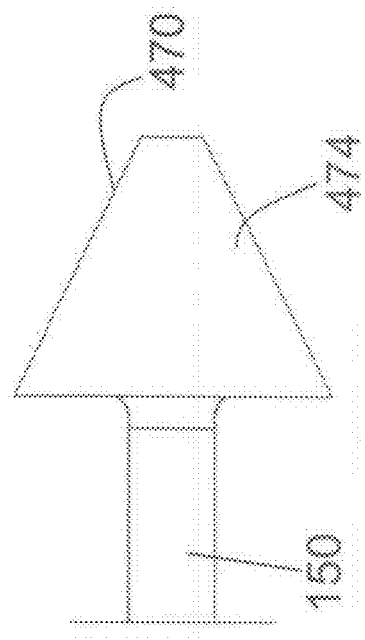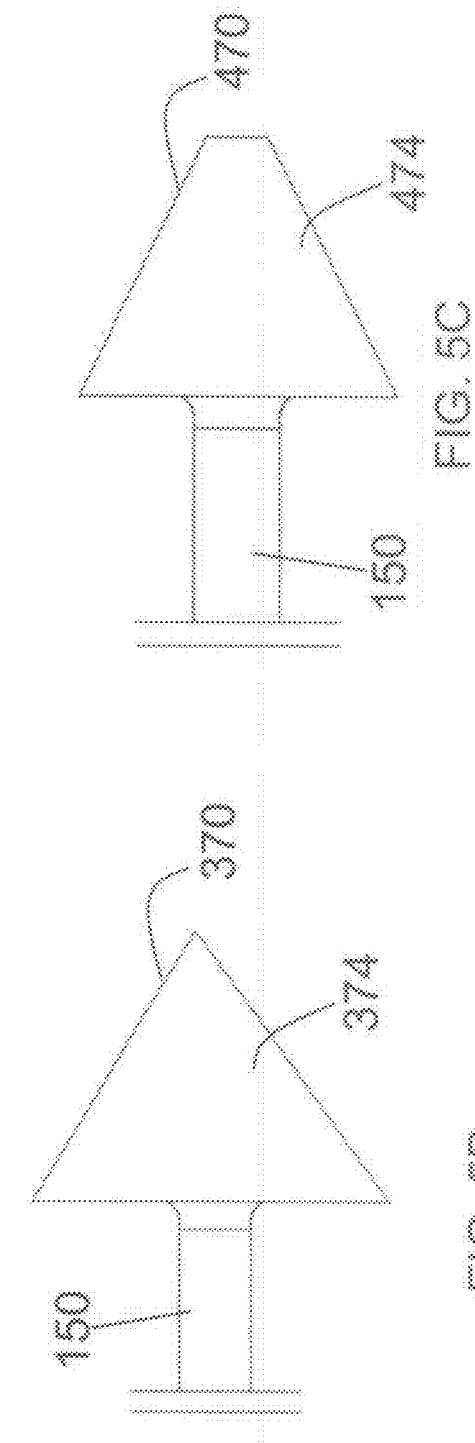

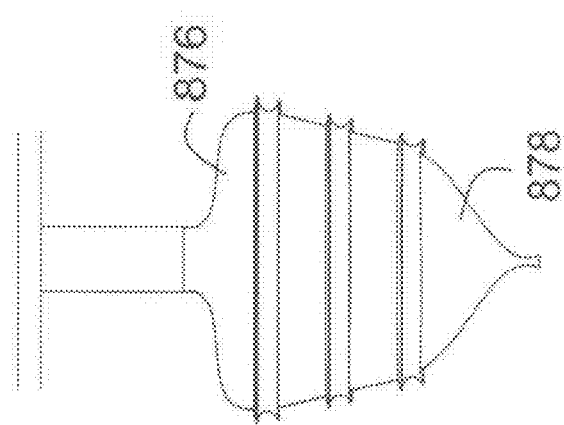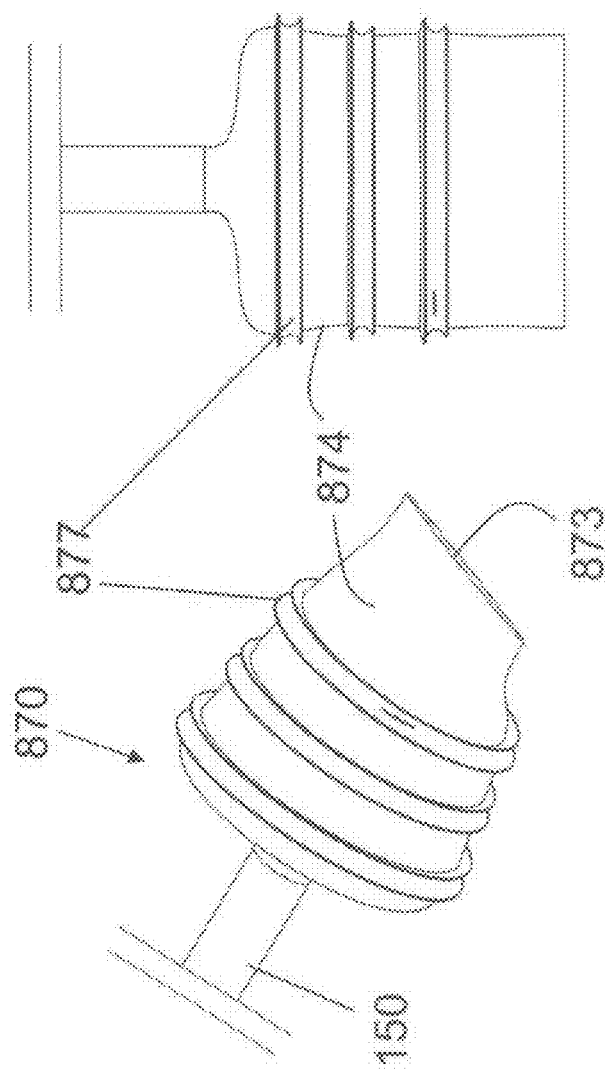

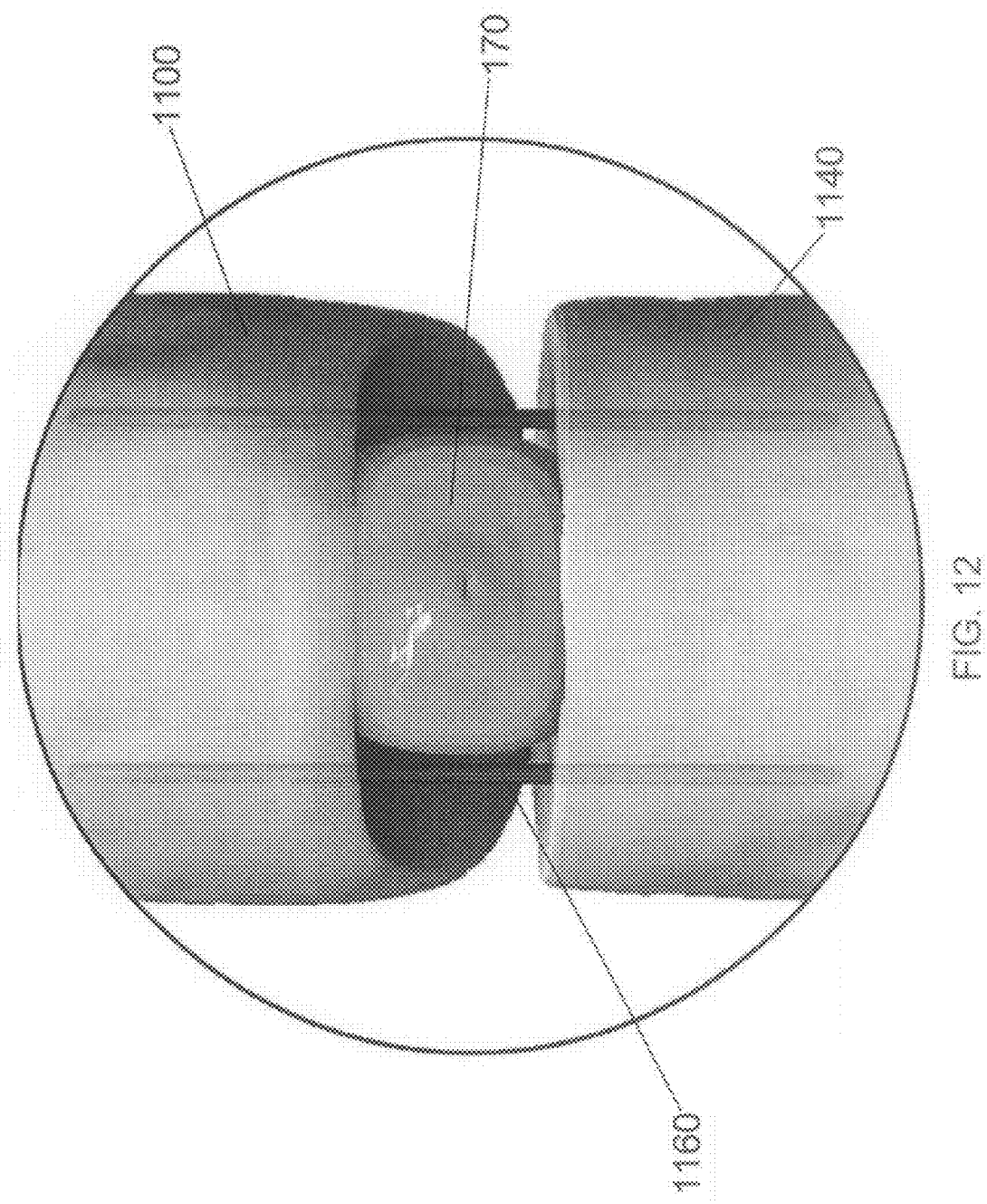

DEVICES AND METHODS FOR BONE ALIGNMENT, STABILIZATION AND DISTRACTION

RELATED APPLICATIONS

This application is a continuation of U.S. patent application Ser. No. 13/617,181, filed Sep. 14, 2012, which is a continuation of U.S. patent application Ser. No. 12/859,680, filed Aug. 19, 2010, now U.S. Pat. No. 8,870,965, which claims the benefit of and priority to U.S. Provisional Patent Application No. 61/235,231, filed on Aug. 19, 2009, the entirety of all these applications are hereby incorporated herein by reference.

FIELD

The embodiments disclosed herein relate to bone implants, and more particularly to devices and methods for bone alignment, stabilization and distraction.

BACKGROUND

Bones form the skeleton of the body and allow the body to be supported against gravity and to move and function in the world. Bone fractures can occur, for example, from an outside force or from a controlled surgical cut (an osteotomy). A fracture's alignment is described as to whether the fracture fragments are displaced or in their normal anatomic position. In some instances, surgery may be required to re-align, stabilize and distract the fractured bone.

SUMMARY

Devices and methods for bone alignment, stabilization and distraction are disclosed herein.

According to aspects illustrated herein, there is provided a bone implant that includes an expandable body having a closed end, a sealable open end, an inner cavity, an external surface and an internal surface, wherein the expandable body has an insertion depth with a fixed dimension, a width with a fixed dimension, and a thickness with a changeable dimension, and wherein entry of a fluid into the inner cavity of the expandable body changes the dimension of the device thickness. In an embodiment, the bone implant of the present disclosure is sufficiently designed to re-align fragments of a fractured bone. In an embodiment, the bone implant of the present disclosure is sufficiently designed to stabilize fragments of a fractured bone. In an embodiment, the bone implant of the present disclosure is sufficiently designed to distract fragments of a fractured bone. In an embodiment, the bone implant of the present disclosure is sufficiently designed to repair angular displacement of a fractured bone. In an embodiment, a bone implant of the present disclosure can be used to restore radial length, volar angulation, and radial inclination for a distal radius fracture with dorsal angulation.

According to aspects illustrated herein, there is provided a bone implant system that includes a light-sensitive liquid; a light source for providing light energy; a light-conducting fiber for delivering the light energy from the light source to cure the light-sensitive liquid; a delivery catheter having a proximal end in communication with the light-conducting fiber and the light-sensitive liquid, an inner lumen for passage of the light-conducting fiber, and an inner void for passage of the light-sensitive liquid; and an expandable body removably engaging a distal end of the delivery catheter, wherein the expandable body has a closed end, a sealable open end, an inner cavity for passage of the light-sensitive liquid, an external surface and an internal surface, wherein the expandable body has an insertion depth with a fixed dimension, a width with a fixed dimension, and a thickness with a changeable dimension, and wherein entry of the light-sensitive liquid into the inner cavity of the expandable body changes the dimension of the device thickness.

According to aspects illustrated herein, there is provided a method of maintaining distraction of a fractured distal radius bone that includes providing temporary distraction to a fractured distal radius bone to provide a distraction gap; delivering an expandable body in an unexpanded state into the distraction gap; infusing a first fluid into the expandable body to expand the expandable body so that a desired amount of distraction is achieved at the distraction gap; removing the first fluid from the expandable body; determining an amount of first fluid removed from the expandable body; infusing an amount of light-sensitive liquid into the expandable body to expand the expandable body, wherein the amount of light-sensitive liquid is substantially equivalent to the amount of first fluid; curing the light-sensitive liquid in the expandable body to form a rigid photodynamic device; and maintaining a desired amount of distraction at the distraction gap.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 2A and FIG. 2B show close-up cross-sectional views of the region circled in FIG. 1. FIG. 2A shows a cross-sectional view of a distal end of the delivery catheter and the expandable body prior to the device being infused with light-sensitive liquid. FIG. 2B shows a cross-sectional view of the distal end of the delivery catheter and the expandable body after the device has been infused with light-sensitive liquid and light energy from the light-conducting fiber is introduced into the delivery catheter and inner lumen of the expandable body to cure the light-sensitive liquid.

FIG. 4A is a schematic illustration showing general properties of an expandable body of the present disclosure. In general, an expandable body of the present disclosure has an insertion depth with a fixed dimension, a width with a fixed dimension, and a thickness with a changeable dimension to provide animal-specific distraction to a fractured bone.

FIG. 4B is a schematic illustration showing the dimensional properties of the expandable body of FIG. 4A with infusion of a fluid into the expandable body.

FIG. 5A is a close-up view of an embodiment of an expandable body of the present disclosure which can be part of the system of FIG. 1. The expandable body is shown in an expanded state.

FIG. 5B is a close-up view of an embodiment of a an expandable body of the present disclosure which can be part of the system of FIG. 1. The expandable body is shown in an expanded state.

FIG. 5C is a close-up view of an embodiment of an expandable body of the present disclosure which can be part of the system of FIG. 1. The expandable body is shown in an expanded state.

FIG. 9A, FIG. 9B and FIG. 9C are close-up views of an embodiment of an expandable body of the present disclosure which can be part of the system of FIG. 1. The expandable body is shown in an expanded state.

FIG. 12 shows a close-up view of an embodiment of a photodynamic device of the present disclosure with ancillary fixation.

Figure 1:
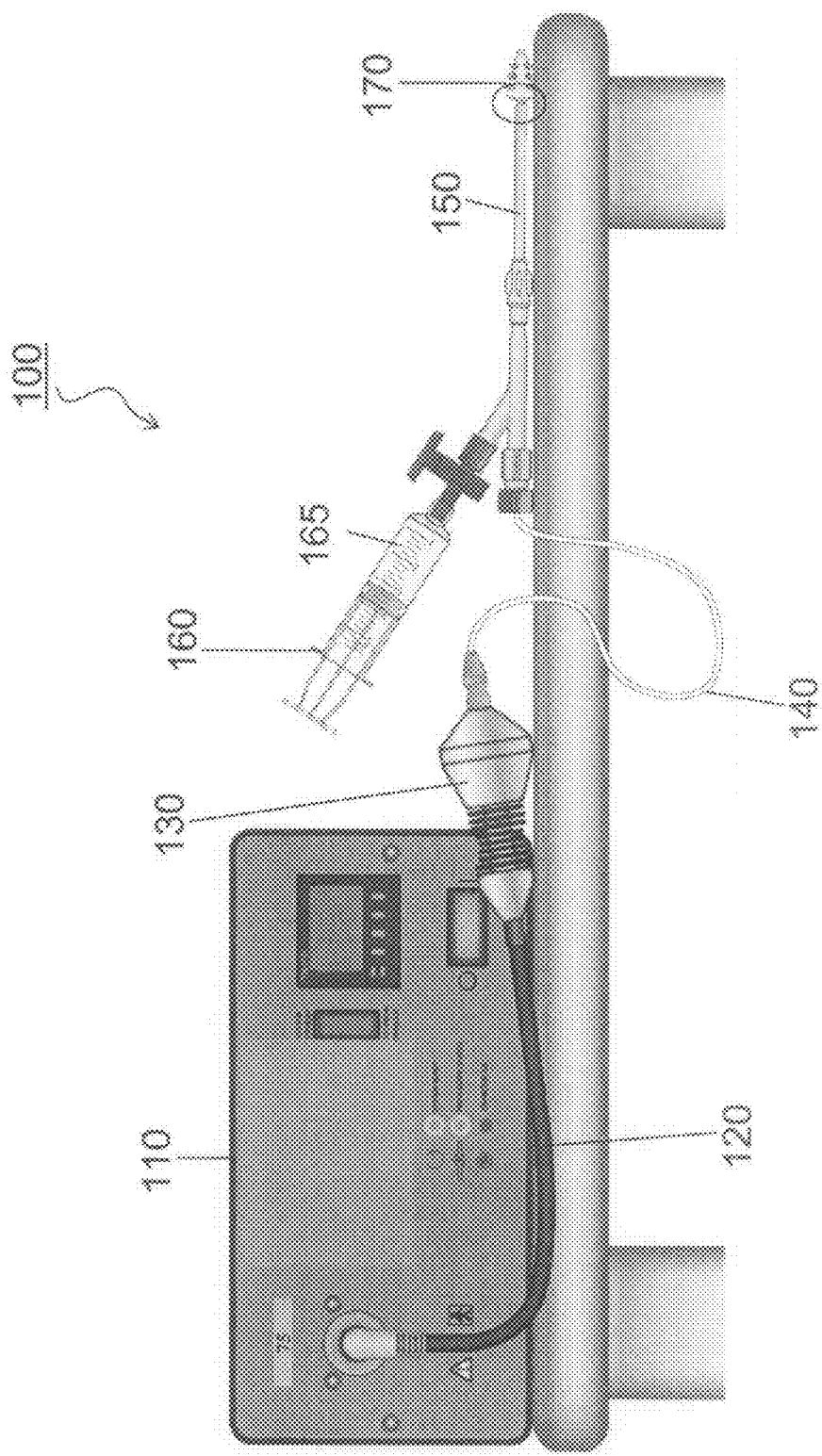
FIG. 1 shows a schematic illustration of an embodiment of a bone implant system of the present disclosure. The system includes a light source, a light pipe, an attachment system, a light-conducting fiber, a light-sensitive liquid, a delivery catheter and an expandable body sufficiently shaped to fit within a space or a gap in a fractured bone.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Devices and methods for bone alignment, stabilization and distraction are disclosed herein. In an embodiment, the present disclosure is directed to devices and methods for human treatment of bone fractures. In an embodiment, the present disclosure is directed to devices and methods for veterinary treatment of bone fractures.

As used herein, the term "animal" means any organism belonging to the kingdom Animalia. In an embodiment, the term "animal" refers to vertebrates, more preferably, mammals including humans. In an embodiment, an expandable body of the present disclosure is implanted in a human. In an embodiment, an expandable body of the present disclosure is implanted in an animal.

As used herein, the terms "fracture" or "fractured bone" refer to a break in the continuity of a bone. The fracture can occur, for example, from an outside force or from a controlled surgical cut (osteotomy). Considerations in fracture care are the fracture's alignment (whether the fracture fragments are displaced or in their normal anatomic position) and angulation. If angulation or displacement is large, reduction (manipulation) of the bone may be required, as well as contact-compression at the fracture surfaces.

As used herein, the term "radius" refers to the bone of the forearm that extends from the lateral side of the elbow to the thumb side of the wrist.

As used herein, the terms "distal radius fracture" and "Colles fracture" refer to a wrist fracture involving a break of the end of the radius.

As used herein, the term "photodynamic device" refers to an expandable body of the present disclosure that is infused with a photodynamic (light curable) material and exposed to an appropriate frequency of light and intensity to cure the material inside the expandable body and form a rigid structure. In an embodiment, the photodynamic device re-aligns a fractured bone. In an embodiment, the photodynamic device stabilizes a fractured bone. In an embodiment, the photodynamic device provides contact-compression at fracture surfaces. In an embodiment, the photodynamic device may be referred to as a "wedge implant" or "bone implant".

As used herein, the term "distraction" refers to positioning a fractured bone back to a substantially normal, anatomically correct, position (separation of the bone fragments). In an embodiment, a photodynamic device of the present disclosure provides distraction to a fractured bone. In an embodiment, a photodynamic device of the present disclosure is used to distract a fractured bone which realigns the fragments to a substantially original position. In an embodiment, a photodynamic device of the present disclosure is used to distract a fractured bone and maintain an angle of the bone which realigns the fragments to a substantially original position. In an embodiment, a photodynamic device of the present disclosure is used to distract a fractured distal radius bone so that a radial tilt of the fractured distal radius is returned to a normal range between about 19° to about 25°. In an embodiment, a photodynamic device of the present disclosure is used to distract a fractured distal radius bone so that a radial length of the fractured distal radius is returned to a normal range between about 9.7 mm to about 17.3 mm. In an embodiment, a photodynamic device of the present disclosure is used to distract a fractured distal radius bone so that a radial length of the fractured distal radius is returned to a normal range of about 12 mm. In an embodiment, a photodynamic device of the present disclosure is used to distract a fractured distal radius bone so that a palmar tilt of the fractured distal radius is returned to a normal range of about 11°. In an embodiment, a photodynamic device of the present disclosure is used to distract a fractured distal radius bone so that a radial tilt of the fractured distal radius is returned to a normal range between about 19° to about 25°, a radial length of the fractured distal radius is returned to a normal range between about 9.7 mm to about 17.3 mm, a radial length of the fractured distal radius is returned to a normal range of about 12 mm, and a palmar tilt of the fractured distal radius is returned to a normal range of about 11°.

As used herein, the term "pullout strength" refers to the force required to pull a photodynamic device of the present disclosure from a fracture site.

FIG. 1 in conjunction with FIG. 2A and FIG. 2B show schematic illustrations of an embodiment of a bone implant system 100 of the present disclosure. System 100 includes a light source 110, a light pipe 120, an attachment system 130 and a light-conducting fiber 140. The attachment system 130 communicates light energy from the light source 110 to the light-conducting fiber 140. In an embodiment, the light source 110 emits frequency that corresponds to a band in the vicinity of 390 nm to 770 nm, the visible spectrum. In an embodiment, the light source 110 emits frequency that corresponds to a band in the vicinity of 410 nm to 500 nm. In an embodiment, the light source 110 emits frequency that corresponds to a band in the vicinity of 430 nm to 450 nm. In an embodiment, the light-conducting fiber 140 is an optical fiber. The optical fiber can be made from any material, such as glass, silicon, silica glass, quartz, sapphire, plastic, combinations of materials, or any other material, and may have any diameter. In an embodiment, the optical fiber is made from a polymethyl methacrylate core with a transparent polymer cladding. The system 100 further includes a flexible delivery catheter 150 having a proximal end that includes at least two ports and a distal end terminating in an expandable body 170. In an embodiment, the expandable body 170 is sufficiently shaped to fit within a space or a gap in a fractured bone. In an embodiment, the expandable body 170 is manufactured from a non-compliant (non-stretch/non-expansion) conformable material. In an embodiment, the expandable body 170 is manufactured from a conformable compliant material that is limited in dimensional change by embedded fibers. One or more radiopaque markers, bands or beads may be placed at various locations along the expandable body 170 and/or the flexible delivery catheter 150 so that components of the system 100 may be viewed using fluoroscopy.

In the embodiment shown in FIG. 1, the proximal end includes two ports. One of the ports can accept, for example, the light-conducting fiber 140. The other port can accept, for example, a syringe 160 housing a light-sensitive liquid 165. In an embodiment, the syringe 160 maintains a low pressure during the infusion and aspiration of the light-sensitive liquid 165. In an embodiment, the syringe 160 maintains a low pressure of about 10 atmospheres or less during the infusion and aspiration of the light-sensitive liquid 165. In an embodiment, the light-sensitive liquid 165 is a photodynamic (light-curable) monomer. In an embodiment, the photodynamic (light-curable) monomer is exposed to an appropriate frequency of light and intensity to cure the monomer inside the expandable body 170 and form a rigid structure. In an embodiment, the photodynamic (light-curable) monomer 165 is exposed to electromagnetic spectrum that is visible (frequency that corresponds to a band in the vicinity of 390 nm to 770 nm). In an embodiment, the photodynamic (light-curable) monomer 165 is radiolucent, which permit x-rays to pass through the photodynamic (light-curable) monomer 165.

As illustrated in FIG. 2A and FIG. 2B, the flexible delivery catheter 150 includes an inner void 152 for passage of the light-sensitive liquid 165, and an inner lumen 154 for passage of the light-conducting fiber 140. In the embodiment illustrated, the inner lumen 154 and the inner void 152 are concentric to one another. The light-sensitive liquid 165 has a low viscosity or low resistance to flow, to facilitate the delivery of the light-sensitive liquid 165 through the inner void 152. In an embodiment, the light-sensitive liquid 165 has a viscosity of about 1000 cP or less. In an embodiment, the light-sensitive liquid 165 has a viscosity ranging from about 650 cP to about 450 cP. The expandable body 170 may be inflated, trial fit and adjusted as many times as a user wants with the light-sensitive liquid 165, up until the light source 110 is activated, when the polymerization process is initiated. Because the light-sensitive liquid 165 has a liquid consistency and is viscous, the light-sensitive liquid 165 may be delivered using low pressure delivery and high pressure delivery is not required, but may be used. In an embodiment, a contrast material may be added to the light-sensitive liquid 165 without significantly increasing the viscosity. Contrast materials include, but are not limited to, barium sulfate, tantalum, or other contrast materials known in the art. The light-sensitive liquid 165 can be introduced into the proximal end of the flexible delivery catheter 150 and passes within the inner void 152 of the flexible delivery catheter 150 up into an inner cavity 172 of the expandable body 170 to change a thickness of the expandable body 170 without changing a width or depth of the expandable body 170. In an embodiment, the light-sensitive liquid 165 is delivered under low pressure via the syringe 160 attached to the port. The light-sensitive liquid 165 can be aspirated and reinfused as necessary, allowing for thickness adjustments to the expandable body 170 prior to activating the light source 110 and converting the liquid monomer 165 into a hard polymer. As illustrated in FIG. 1 in conjunction with FIG. 2B, the light-conducting fiber 140 can be introduced into the proximal end of the flexible delivery catheter 150 and passes within the inner lumen 154 of the flexible delivery catheter 150 up into the expandable body 170. The light-sensitive liquid 165 remains a liquid monomer until activated by the light-conducting fiber 140 (cures on demand). Radiant energy from the light source 110 is absorbed and converted to chemical energy to polymerize the monomer. The light-sensitive liquid 165, once exposed to the correct frequency light and intensity, is converted into a hard polymer, resulting in a rigid structure or photodynamic device of the present disclosure. In an embodiment, the monomer 165 cures in about five seconds to about five minutes. This cure affixes the expandable body 170 in an expanded shape to form a photodynamic device of the present disclosure. A cure may refer to any chemical, physical, and/or mechanical transformation that allows a composition to progress from a form (e.g., flowable form) that allows it to be delivered through the inner void 162 in the flexible delivery catheter 150, into a more permanent (e.g., cured) form for final use in vivo. For example, "curable" may refer to uncured light-sensitive liquid 165, having the potential to be cured in vivo (as by catalysis or the application of a suitable energy source), as well as to a light-sensitive liquid 165 in the process of curing (e.g., a composition formed at the time of delivery by the concurrent mixing of a plurality of composition components). In an embodiment, the photodynamic device can re-align a fractured bone. In an embodiment, the photodynamic device can provide stabilization to a fractured bone. In an embodiment, the photodynamic device can provide distraction to a fractured bone. In an embodiment, the photodynamic device can provide contact-compression at fracture surfaces.

In an embodiment, a photodynamic device of the present disclosure can provide internal bone alignment, stabilization, and/or distraction to fractures, including, but not limited to, fractures of the hand and wrist (including, but not limited to the metacarpal bones), the forearm (including, but not limited to, the radius and ulna), the face or jaw, the foot and ankle (including, but not limited to, the metatarsal bones, the cuneiform bones, and the calcaneus bone), the pelvic area, the leg (including, but not limited to, the tibia), and other areas of the skeletal system that require angular correction. In an embodiment, a photodynamic device of the present disclosure is sufficiently designed to re-align fragments of a fractured bone. In an embodiment, a photodynamic device of the present disclosure is sufficiently designed to stabilize fragments of a fractured bone. In an embodiment, a photodynamic device of the present disclosure is sufficiently designed to distract fragments of a fractured bone. In an embodiment, a photodynamic device of the present disclosure is sufficiently designed to repair angular displacement of a fractured bone. In an embodiment, a photodynamic device of the present disclosure can provide internal bone alignment, stabilization and/or distraction of a distal radius fracture. In an embodiment, a photodynamic device of the present disclosure can provide internal bone alignment, stabilization and/or distraction of a metatarsal fracture. In an embodiment, a photodynamic device of the present disclosure can provide internal bone alignment, stabilization and/or distraction of a distal osteotomy of the first metatarsal to treat hallux valgus (bunion). In an embodiment, a photodynamic device of the present disclosure is used to align, stabilize and/or distract a wedge osteotomy of the foot. In an embodiment, a photodynamic device of the present disclosure is used during an Evans calcaneal osteotomy procedure for lateral column lengthening. In an embodiment, a photodynamic device of the present disclosure is used during a plantarflexion opening wedge medial cuneiform (Cotton) osteotomy procedure. In an embodiment, a photodynamic device of the present disclosure is used during a wedge osteotomy and stabilization of the wrist in a distal radius procedure. In an embodiment, a photodynamic device of the present disclosure is used in an open wedge osteotomy.

A common fracture, especially in the older population, is a fracture of the distal radius. This type of fracture usually results from a fall upon an outstretched hand. A fracture of the distal radius often results in parts of the wrist folding on each other which results in severe angulation of the wrist. Due to the shape of the distal radius after a fracture, as well as the lack of space and the number of tendons and nerves in the fractured area, treatment of a distal radius fracture is often complicated.

Distal radius fractures typically occur at the cortico-cancellous junction at the distal end of the radius. Fractures of the distal radius are most commonly caused by people falling forward onto a hard surface and breaking their fall with extended outstretched hands. Since 80% of the load through the wrist joint is carried by the radius it is not surprising that the fracture occurs at this junction. These fractures are the most commonly occurring fractures in adults and one out of six fractures seen in the emergency room is of this type. An anatomic description of the distal radius fracture is the easiest way to describe the fracture, decide on treatment, and make an assessment of stability. These descriptions may include an assessment of articular incongruity, radial shortening, radial angulation, comminution of the fracture (the amount of crumbling at the fracture site), and open (compound) or closed injury. The assessment may also involve other associated ulnar styloid fractures or soft tissue injuries. A distal radius fracture is often difficult to treat. This is, in part, due to the shape of the distal radius after an injury, the lack of space within the distal radius and the number of tendons and nerves in the area. When surgical treatment of a fracture is performed, it is usually done by open reduction and internal fixation with plate, rods and/or screws. If the fracture is unstable the deformity at the fracture site will increase and cause limitation of wrist motion and forearm rotation, pronation and supination. If the joint surface is damaged and heals with more than 1 mm to 2 mm of unevenness, the wrist joint will be prone to post-traumatic osteoarthritis. In an embodiment, a photodynamic device of the present disclosure is sufficiently designed to re-align fragments of a fractured distal radius bone. In an embodiment, a photodynamic device of the present disclosure is sufficiently designed to stabilize fragments of a fractured bone distal radius bone. In an embodiment, a photodynamic device of the present disclosure is sufficiently designed to distract fragments of a fractured distal radius bone. In an embodiment, a photodynamic device of the present disclosure is sufficiently designed to repair angular displacement of a fractured distal radius bone. In an embodiment, a photodynamic device of the present disclosure can be used to restore radial length, volar angulation, and radial inclination for a distal radius fracture with angulation.

Figure 3B:
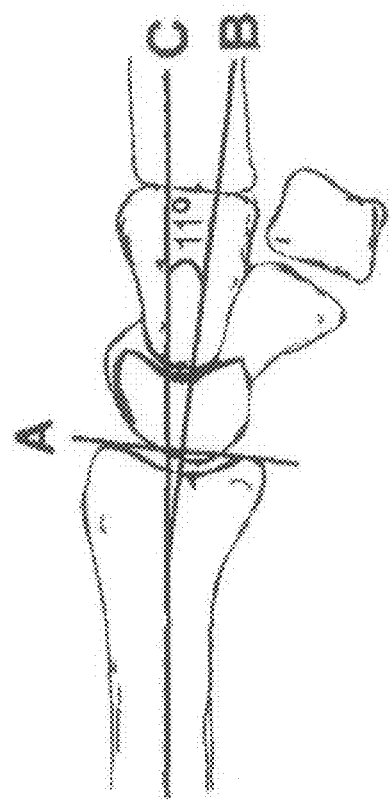
FIG. 3B is a schematic illustration of the measurement of the palmar angulation of a radius.
Figure 3A:
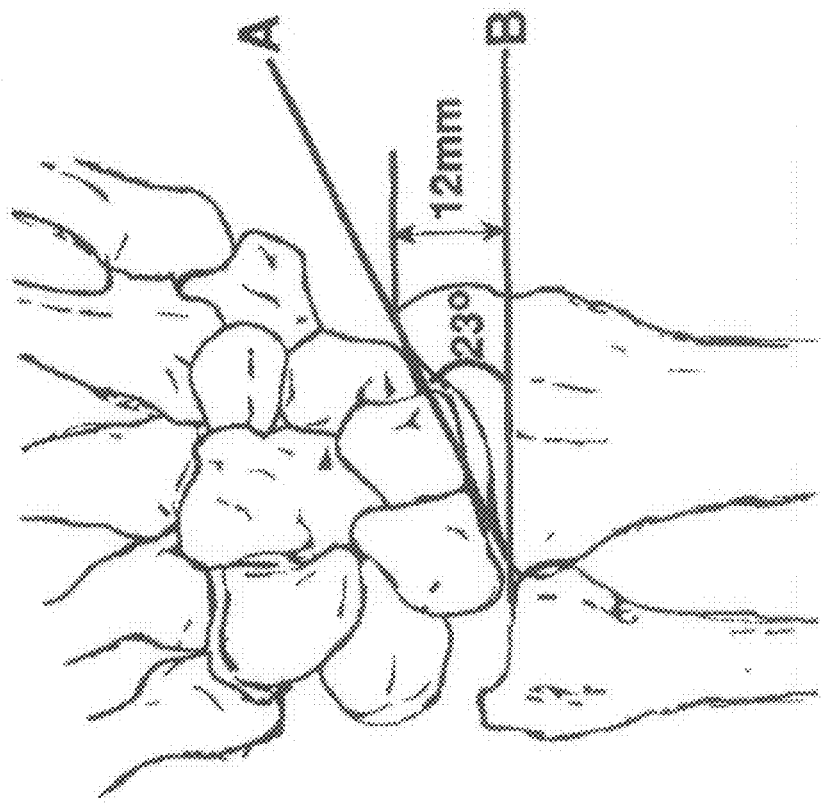
FIG. 3A is a schematic illustration of the measurement of the average radial angle and radial length at the left human wrist.

FIG. 3A is a schematic illustration of the measurement of the average radial angle and radial length at the left human wrist. A, Line drawn from the tip of the radial styloid to the articular surface of the ulnar fossa. B, Line drawn perpendicular to the long axis of the radius. The angle between lines A and B (here 23°, normal range between about 19° to about 25°) is defined as the radial inclination angle (syn.: radial deviation, ulnar inclination, radial tilt, radial angulation). The distance between B and the tip of the radial styloid (here 12 mm, normal range between about 9.7 mm to about 17.3 mm) is known as the radial length (syn.: radial height, length of the radial styloid).

FIG. 3B is a schematic illustration of the measurement of the palmar angulation. A, Line drawn from the dorsal lip to the palmar lip of the distal radius. B, Line perpendicular to A. C, Line parallel to the long axis of the radius. The angle between lines B and C (here 11°) is defined as palmar tilt (syn.: palmar slope, volar tilt).

FIG. 4A is a schematic illustration showing general properties of an expandable body 170 of the present disclosure. In general, expandable body 170 has an insertion depth with a fixed dimension, a width with a fixed dimension, and a thickness with a changeable dimension to provide appropriate distraction to a bone, wherein entry of a fluid into the inner cavity 172 of the expandable body 170 changes the dimension of the device thickness. The insertion depth and the width are fixed dimensions, and are not affected by the infusion of fluid into the expandable body 170. In general, and shown in the embodiment illustrated in FIG. 2A in conjunction with FIG. 4A, the expandable body 170 includes a closed end 173, a sealable open end 175, an inner cavity 172, an external surface 174 and an internal surface 176. The fluid that can be infused into the inner cavity 172 of the expandable body 170 includes, but is not limited to, air and light-sensitive liquid 165.

In an embodiment, the expandable body 170 is thicker at a proximal area 176 (the area engaging the delivery catheter 150) and tapers in thickness as it approaches a distal area 178. A distal area 178 that tapers may allow for easier insertion of the expandable body 170. In an embodiment, the expandable body 170 has a proximal area 176 and a distal area 178 that is generally constant in thickness. In an embodiment, the thickness of the expandable body 170 may decrease along the depth of the expandable body 170 traveling from the proximal area 176 to the distal area 178. The selection of the appropriate shape and size of the expandable body 170 may be based on the type, size and location of the injury as well as the treatment goals.

The dimensions of the proximal area 176, including the depth, width, diameter or thickness, may vary based on the shape of the proximal area 176. In an embodiment, the depth of the proximal area 176 may range from about 10 mm to about 25 mm. In an embodiment, the width of the proximal area 176 may range from about 8 mm to about 25 mm. In an embodiment, the thickness of the proximal area 176 may range from about 2 mm to about 25 mm. It should be appreciated that these dimensions are only provided as examples. The dimensions of the proximal area 176 can be smaller or larger as the present disclosure is not intended to be limited in this manner.

The dimensions of the distal area 178, including the depth, width, diameter or thickness, may vary based on the shape of the distal area 178. In an embodiment, the depth of the distal area 178 may range from about 10 mm to about 25 mm. In an embodiment, the width of the distal area 178 may range from about 8 mm to about 25 mm. In an embodiment, the thickness of the distal area 178 may range from about 2 mm to about 25 mm. It should be appreciated that these dimensions are only provided as examples. The dimensions of the distal area 178 can be smaller or larger as the present disclosure is not intended to be limited in this manner.

An expandable body 170 of the present disclosure can be infused with light-sensitive liquid 165 such that the final cured photodynamic device provides distraction of about 1 mm to bone fragments. An expandable body 170 of the present disclosure can be infused with light-sensitive liquid 165 such that the final cured photodynamic device provides distraction of about 2 mm to bone fragments. An expandable body 170 of the present disclosure can be infused with light-sensitive liquid 165 such that the final cured photodynamic device provides distraction of about 3 mm to bone fragments. An expandable body 170 of the present disclosure can be infused with light-sensitive liquid 165 such that the final cured photodynamic device provides distraction of about 4 mm to bone fragments. An expandable body 170 of the present disclosure can be infused with light-sensitive liquid 165 such that the final cured photodynamic device provides distraction of about 5 mm to bone fragments. An expandable body 170 of the present disclosure can be infused with light-sensitive liquid 165 such that the final cured photodynamic device provides distraction of about 6 mm to bone fragments. An expandable body 170 of the present disclosure can be infused with light-sensitive liquid 165 such that the final cured photodynamic device provides distraction of about 7 mm to bone fragments. An expandable body 170 of the present disclosure can be infused with light-sensitive liquid 165 such that the final cured photodynamic device provides distraction of about 8 mm to bone fragments. An expandable body 170 of the present disclosure can be infused with light-sensitive liquid 165 such that the final cured photodynamic device provides distraction of about 9 mm to bone fragments. An expandable body 170 of the present disclosure can be infused with light-sensitive liquid 165 such that the final cured photodynamic device provides distraction of about 10 mm to bone fragments. An expandable body 170 of the present disclosure can be infused with light-sensitive liquid 165 such that the final cured photodynamic device provides distraction of about 11 mm to bone fragments. An expandable body 170 of the present disclosure can be infused with light-sensitive liquid 165 such that the final cured photodynamic device provides distraction of about 12 mm to bone fragments. Therefore, the expandable body 170 of the present disclosure is capable of providing customized distraction—angulation correction specific to a patient.

FIG. 4B is a schematic illustration showing the dimensional properties of the expandable body 170 of FIG. 4A with infusion of the light-sensitive liquid 165 into the expandable body 170. Modification of light-sensitive liquid 165 infusion allows a user to adjust the span or thickness of expandable body 170 to customize the angulation and distraction of the expandable body 170 to provide specific expandable body 170 size and shape to the animal. In that the expandable body 170 is formable and shapeable by the user prior to the photo-curing of the light-sensitive liquid 165 in the expandable body 170, the resultant implant best mirrors the size and shape of the area that the implant is stabilizing, and that the shape attempts to maximize the surface contact area, minimizing specific points of concentrated pressure. The implant design provides excellent compressive strength, thus minimizing deformation under dynamic loading conditions. The implant has a compressive modulus that is close to that of cancellous bone, allowing the natural transfer of dynamic loads away from the implant to the surrounding bone.

In an embodiment, the external surface 174 of the expandable body 170 is resilient and puncture resistant. In an embodiment, the expandable body 170 is manufactured from a non-compliant (non-stretch/non-expansion) conformable material including but not limited to urethane, polyethylene terephthalate (PET), nylon elastomer and other similar polymers. In an embodiment, the expandable body 170 is manufactured from a polyethylene terephthalate (PET). In an embodiment, the expandable body 170 is manufactured from a radiolucent material, which permit x-rays to pass through the expandable body 170. In an embodiment, the expandable body 170 is manufactured from a radiolucent polyethylene terephthalate (PET). In an embodiment, the expandable body 170 is manufactured from a conformable compliant material that is limited in dimensional change by embedded fibers. In an embodiment, at least a portion of the external surface 174 of the expandable body 170 is substantially even and smooth. In an embodiment, at least a portion of the external surface 174 of the expandable body 170 includes at least one textured element 177 such as a bump, a ridge, a rib, an indentation or any other shape. In an embodiment, at least a portion of the external surface 174 of the expandable body 170 protrudes out to form a textured element 177. In an embodiment, at least a portion of the external surface 174 of the expandable body 170 invaginates to form a textured element 177. In an embodiment, the textured element 177 increases the friction and improves the grip and stability of the expandable body 170 after the expandable body 170 is inserted into the fracture location. In an embodiment, the textured element 177 results in increased interdigitation of bone-device interface as compared to an expandable body without textured elements. In an embodiment, the textured element 177 can be convex in shape. In an embodiment, the textured element 177 can be concave in shape. In an embodiment, the textured element 177 can be circumferential around the width of the expandable body 170, either completely or partially.

In general, bone graft or bone graft substitute can be used in conjunction with an expandable body 170 of the present disclosure. In an embodiment, the bone graft is an allogeneic bone graft. In an embodiment, the bone graft is an autologous bone graft. In an embodiment, the bone graft substitute is a hydroxyapatite bone substitute. In an embodiment, a bone graft or bone graft substitute is used to fill in any gaps that may exist, for example, between the external surface 174 of the expandable body 180 and the surfaces of the bone fragments. In an embodiment, a bone graft or bone graft substitute is used to fill any gaps that may exist, for example, between the textured element 177 of the expandable body 180 and the surfaces of the bone fragments.

In general, the expandable body 170 can include an external surface that may be coated with materials including, but not limited to, drugs (for example, antibiotics), proteins (for example, growth factors) or other natural or synthetic additives (for example, radiopaque or ultrasonically active materials). For example, after a minimally invasive surgical procedure an infection may develop in a patient, requiring the patient to undergo antibiotic treatment. An antibiotic drug may be added to the external surface of the expandable body 170 to prevent or combat a possible infection. Proteins, such as, for example, bone morphogenic protein or other growth factors have been shown to induce the formation of cartilage and bone. A growth factor may be added to the external surface of the expandable body 170 to help induce the formation of new bone. Due to the lack of thermal egress of the light-sensitive liquid 165 in the expandable body 170, the effectiveness and stability of the coating is maintained.

In general, the expandable body 170 typically does not have any valves. One benefit of having no valves is that the expandable body 170 may be expanded or reduced in size as many times as necessary to assist in the fracture reduction and placement. Another benefit of the expandable body 170 having no valves is the efficacy and safety of the system 100. Since there is no communication passage of light-sensitive liquid 165 to the body there cannot be any leakage of liquid 165 because all the liquid 165 is contained within the expandable body 170. In an embodiment, a permanent seal is created between the expandable body 170 and the delivery catheter 150 that is both hardened and affixed prior to the delivery catheter 150 being removed.

In an embodiment, abrasively treating the external surface 174 of the expandable body 170 for example, by chemical etching or air propelled abrasive media, improves the connection and adhesion between the external surface 174 of the expandable body 170 and a bone surface. The surfacing significantly increases the amount of surface area that comes in contact with the bone which can result in a stronger grip.

Various embodiments of expandable body's of the present disclosure will now be discussed. In general, an expandable body of the present disclosure can include any of the features described above, with modification to some or all of the features.

FIG. 5A is a close-up view of an embodiment of an expandable body 270 having an acorn shape of the present disclosure which can be part of the system 100 of FIG. 1. FIG. 5B is a close-up view of an embodiment of a an expandable body 370 having a triangular shape of the present disclosure which can be part of the system 100 of FIG. 1. FIG. 5C is a close-up view of an embodiment of an expandable body 470 having a trapezoidal shape of the present disclosure which can be part of the system 100 of FIG. 1. The expandable body 270, 370 and 470 are shown in an expanded state. The expandable body 270, 370 and 470 includes a closed end, a sealable open end, an inner cavity (not visible), an external surface 274, 374 and 474, and an internal surface (not visible). The fluid that can be infused into the inner cavity of the expandable body 270, 370 and 470 includes, but is not limited to, air and light-sensitive liquid 165. Expandable body 270, 370 and 470 has an insertion depth with a fixed dimension, a width with a fixed dimension, and a thickness with a changeable dimension to provide appropriate distraction to a bone, wherein entry of a fluid into the inner cavity of the expandable body 270, 370 and 470 changes the dimension of the expandable body 270, 370 and 470 thickness or distraction that the hardened expandable body 270, 370 and 470 provides. The insertion depth and the width are fixed dimensions, and are not affected by the infusion of fluid into the expandable body 270, 370 and 470. Modification of light-sensitive liquid 165 infusion allows a user to adjust the span or thickness of the expandable body 270, 370 and 470 to customize the angulation and distraction of the expandable body 270, 370 and 470 to provide a user-specific size and shape for the animal. In that the expandable body 270, 370 and 470 is formable and shapeable by the surgeon prior to the photocuring of the light-sensitive liquid 165 in the expandable body 270, 370 and 470, the resultant implant best mirrors the size and shape of the area that the implant is stabilizing, and that the shape attempts to maximize the surface contact area, minimizing specific points of concentrated pressure. In an embodiment, the expandable body 270, 370 and 470 design provides excellent compressive strength, thus minimizing deformation under dynamic loading conditions. The implant has a compressive modulus that is close to that of cancellous bone, allowing the natural transfer of dynamic loads away from the implant to the surrounding bone.

In an embodiment, the external surface 274, 374 and 474 of the expandable body 270, 370 and 470 is resilient and puncture resistant. In an embodiment, the expandable body 270, 370 and 470 is manufactured from a non-compliant (non-stretch/non-expansion) conformable material including but not limited to urethane, polyethylene terephthalate (PET), nylon elastomer and other similar polymers. In an embodiment, the expandable body 270, 370 and 470 is manufactured from a polyethylene terephthalate In the embodiments illustrated in FIG. 5A, FIG. 5B and FIG. 5C, the expandable body 270, 370 and 470 are without textured surfaces. In an embodiment, the pullout strength for a hardened expandable body 270, 370 and 470 having no textured surfaces is between approximately 0 Newtons and about 20 Newtons. In an embodiment, the pullout strength for a hardened expandable body 270, 370 and 470 having no textured surfaces is about 6 Newtons.

Figure 6B:
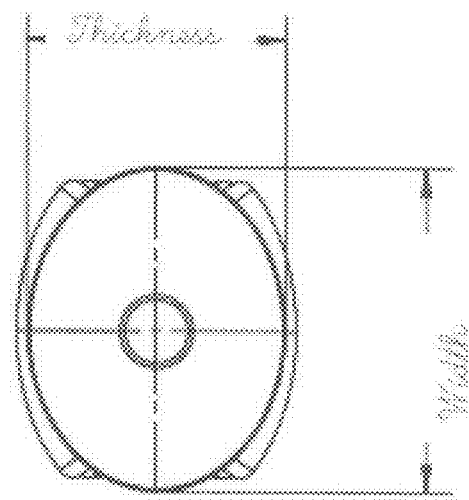
FIG. 6A and FIG. 6B are close-up views of an embodiment of an expandable body of the present disclosure which can be part of the system of FIG. 1. The expandable body is shown in an expanded state.
Figure 6A:
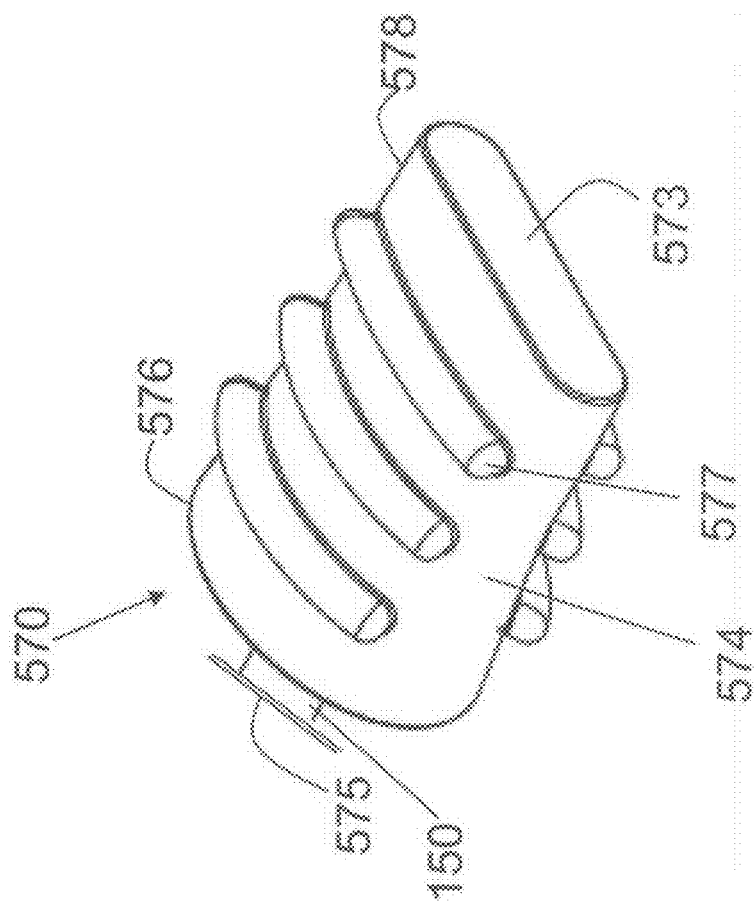

FIG. 6A and FIG. 6B are close-up views of an embodiment of an expandable body 570 of the present disclosure which can be part of the system 100 of FIG. 1. The expandable body 570 is shown in an expanded state. The expandable body 570 includes a closed end 573, a sealable open end 575, an inner cavity (not visible), an external surface 574 and an internal surface (not visible). The fluid that can be infused into the inner cavity of the expandable body 570 includes, but is not limited to, air and light-sensitive liquid 165. Expandable body 570 has an insertion depth with a fixed dimension, a width with a fixed dimension, and a thickness with a changeable dimension to provide appropriate distraction to a bone, wherein entry of a fluid into the inner cavity of the expandable body 570 changes the dimension of the expandable body 570 thickness or distraction that the hardened expandable body 570 provides. The insertion depth and the width are fixed dimensions, and are not affected by the infusion of fluid into the expandable body 570. Modification of light-sensitive liquid 165 infusion allows a user to adjust the span or thickness of the expandable body 570 to customize the angulation and distraction of the expandable body 570 to provide a user-specific size and shape for the animal. In that the expandable body 570 is formable and shapeable by the surgeon prior to the photocuring of the light-sensitive liquid 165 in the expandable body 570, the resultant implant best mirrors the size and shape of the area that the implant is stabilizing, and that the shape attempts to maximize the surface contact area, minimizing specific points of concentrated pressure. In an embodiment, the expandable body 570 design provides excellent compressive strength, thus minimizing deformation under dynamic loading conditions. The implant has a compressive modulus that is close to that of cancellous bone, allowing the natural transfer of dynamic loads away from the implant to the surrounding bone.

In an embodiment, the external surface 574 of the expandable body 570 is resilient and puncture resistant. In an embodiment, the expandable body 570 is manufactured from a non-compliant (non-stretch/non-expansion) conformable material including but not limited to urethane, polyethylene terephthalate (PET), nylon elastomer and other similar polymers. In an embodiment, the expandable body 570 is manufactured from a polyethylene terephthalate (PET).

As illustrated in FIG. 6A and FIG. 6B, at least a portion of the external surface 574 of the expandable body 570 is substantially even and smooth and at least a portion of the external surface 574 of the expandable body 570 includes a plurality of textured elements 577 or bumps. In an embodiment, the plurality of textured elements 577 improves the grip and stability of the expandable body 570 after the expandable body 570 is inserted into the fracture or osteotomy location. The plurality of textured elements 577 are positioned on a top face and a bottom face of the external surface 574. The plurality of textured elements 577 are not contiguous or circumferential, ensuring that the expansion/filling of the expandable body 570 causes the expandable body 570 to expand in diameter, rather than to expand in length. The expandable body 570 is thicker at a proximal area 576 (the area engaging the delivery catheter 150) and tapers in thickness as it approaches a distal area 578. A distal area 578 that tapers may allow for easier insertion of the expandable body 570.

Figure 7B:
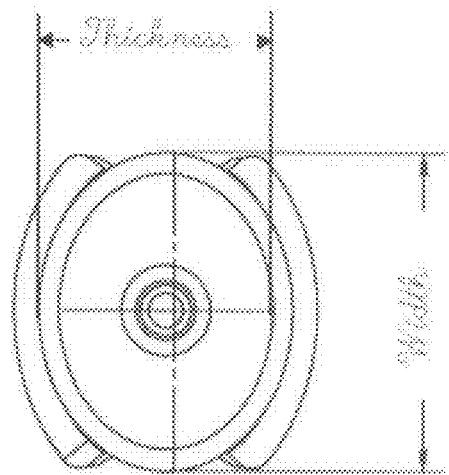
FIG. 7A and FIG. 7B are close-up views of an embodiment of an expandable body of the present disclosure which can be part of the system of FIG. 1. The expandable body is shown in an expanded state.
Figure 7A:
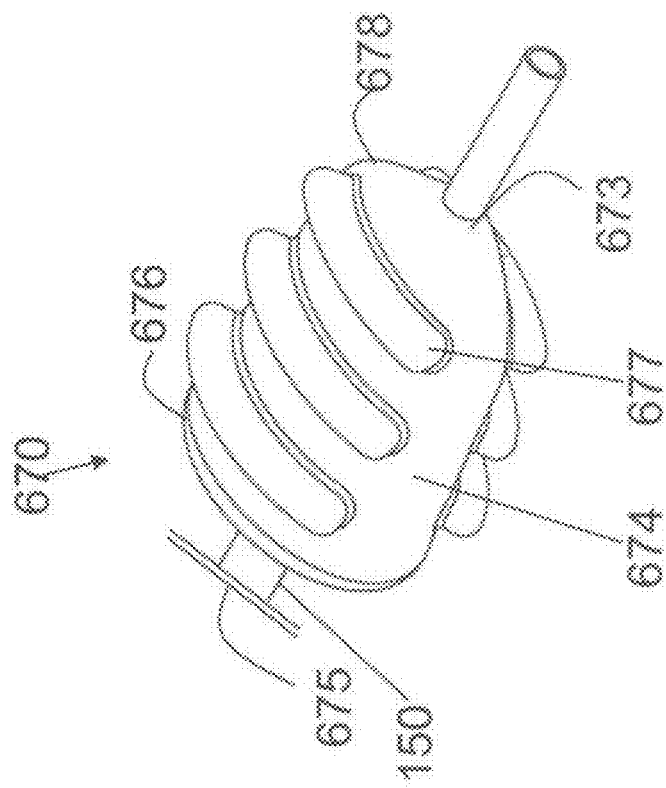

FIG. 7A and FIG. 7B are close-up views of an embodiment of an expandable body 670 of the present disclosure which can be part of the system 100 of FIG. 1. The expandable body 670 is shown in an expanded state. The expandable body 670 has a closed end 673, a sealable open end 673, an inner cavity (not visible), an external surface 674 and an internal surface (not visible). The fluid that can be infused into the inner cavity of the expandable body 670 includes, but is not limited to, air and light-sensitive liquid 165. Expandable body 670 has an insertion depth with a fixed dimension, a width with a fixed dimension, and a thickness with a changeable dimension, wherein entry of a fluid into the inner cavity of the expandable body 670 changes the dimension of the expandable body 670 thickness or distraction that the hardened expandable body 670 provides. The insertion depth and the width are fixed dimensions, and are not affected by the infusion of fluid into the expandable body 670. Modification of light-sensitive liquid 165 infusion allows a user to adjust the span or thickness of the expandable body 670 to customize the angulation and distraction of the expandable body 670 to provide a user-specific size and shape for the animal. In that the expandable body 670 is formable and shapeable by the surgeon prior to the photocuring of the light-sensitive liquid 165 in the expandable body 670, the resultant implant best mirrors the size and shape of the area that the implant is stabilizing, and that the shape attempts to maximize the surface contact area, minimizing specific points of concentrated pressure. In an embodiment, the expandable body 670 design provides excellent compressive strength, thus minimizing deformation under dynamic loading conditions. The implant has a compressive modulus that is close to that of cancellous bone, allowing the natural transfer of dynamic loads away from the implant to the surrounding bone.

In an embodiment, the external surface 674 of the expandable body 670 is resilient and puncture resistant. In an embodiment, the expandable body 670 is manufactured from a non-compliant (non-stretch/non-expansion) conformable material including but not limited to urethane, polyethylene terephthalate (PET), nylon elastomer and other similar polymers. In an embodiment, the expandable body 670 is manufactured from a polyethylene terephthalate (PET).

As illustrated in FIG. 7A and FIG. 7B, at least a portion of the external surface 674 of the expandable body 670 is substantially even and smooth and at least a portion of the external surface 674 of the expandable body 670 includes a plurality of textured elements 677 or bumps. In an embodiment, the plurality of textured elements 677 improves the grip and stability of the expandable body 670 after the expandable body 670 is inserted into the fracture or osteotomy location. The plurality of textured elements 677 are positioned on a top face and a bottom face of the external surface 674. The plurality of textured elements 677 are not contiguous or circumferential, ensuring that the expansion/filling of the expandable body 670 causes the expandable body 670 to expand in diameter, rather than to expand in length. The expandable body 670 is thicker at a proximal area 676 (the area engaging the delivery catheter 150) and tapers in thickness as it approaches a distal area 678. A distal area 68 that tapers may allow for easier insertion of the expandable body 670.

Figures 8A, 8B, 8C:
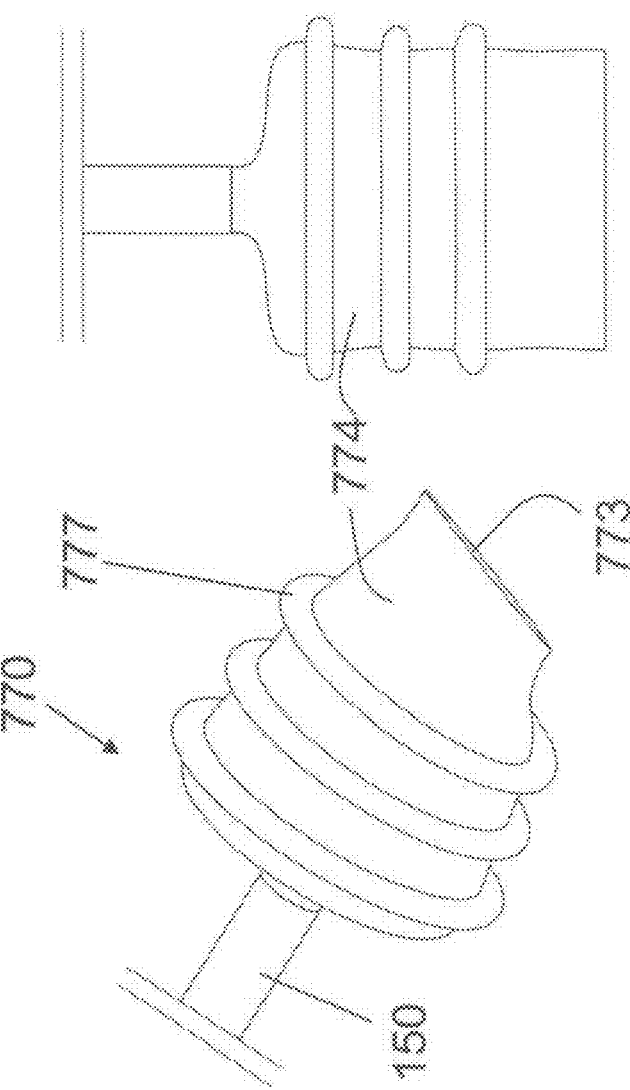
FIG. 8A, FIG. 8B and FIG. 8C are close-up views of an embodiment of an expandable body of the present disclosure which can be part of the system of FIG. 1. The expandable body is shown in an expanded state.

FIG. 8A, FIG. 8B and FIG. 8C are close-up views of an embodiment of an expandable body 770 of the present disclosure which can be part of the system 100 of FIG. 1. The expandable body 770 is shown in an expanded state. The expandable body 770 includes a closed end 773, a sealable open end 775, an inner cavity (not visible), an external surface 774 and an internal surface (not visible). The fluid that can be infused into the inner cavity of the expandable body 770 includes, but is not limited to, air and light-sensitive liquid 165. Expandable body 770 has an insertion depth with a fixed dimension, a width with a fixed dimension, and a thickness with a changeable dimension to provide appropriate distraction to a bone, wherein entry of a fluid into the inner cavity of the expandable body 770 changes the dimension of the expandable body 770 thickness or distraction that the hardened expandable body 770 provides. The insertion depth and the width are fixed dimensions, and are not affected by the infusion of fluid into the expandable body 770. Modification of light-sensitive liquid 165 infusion allows a user to adjust the span or thickness of the expandable body 770 to customize the angulation and distraction of the expandable body 770 to provide a user-specific size and shape for the animal. In that the expandable body 770 is formable and shapeable by the surgeon prior to the photocuring of the light-sensitive liquid 165 in the expandable body 770, the resultant implant best mirrors the size and shape of the area that the implant is stabilizing, and that the shape attempts to maximize the surface contact area, minimizing specific points of concentrated pressure. In an embodiment, the expandable body 770 design provides excellent compressive strength, thus minimizing deformation under dynamic loading conditions. The implant has a compressive modulus that is close to that of cancellous bone, allowing the natural transfer of dynamic loads away from the implant to the surrounding bone.

In an embodiment, the external surface 774 of the expandable body 770 is resilient and puncture resistant. In an embodiment, the expandable body 770 is manufactured from a non-compliant (non-stretch/non-expansion) conformable material including but not limited to urethane, polyethylene terephthalate (PET), nylon elastomer and other similar polymers. In an embodiment, the expandable body 770 is manufactured from a polyethylene terephthalate (PET).

As illustrated in FIG. 8A, FIG. 8B and FIG. 8C, at least a portion of the external surface 774 of the expandable body 770 is substantially even and smooth and at least a portion of the external surface 774 of the expandable body 770 includes a plurality of textured elements 777 or convex ribs that completely surround the external surface 774. In an embodiment, the expandable body 770 includes one, two, three, four, five, six, seven, eight, nine, ten or more than ten convex ribs. In an embodiment, each convex rib may be between about 2 mm and about 5 mm in width. In an embodiment, the convex ribs may each be substantially the same width. In an embodiment, the convex ribs may be of varying width. In an embodiment, the plurality of textured elements 777 improves the grip and stability of the expandable body 770 after the expandable body 770 is inserted into the fracture or osteotomy location. The expandable body 770 is thicker at a proximal area 776 (the area engaging the delivery catheter 150) and tapers in thickness as it approaches a distal area 778. A distal area 778 that tapers may allow for easier insertion of the expandable body 770. In an embodiment, the pullout strength for the hardened expandable body 770 having convex ribs is between approximately 80 Newtons and about 140 Newtons. In an embodiment, the pullout strength for the hardened expandable body 770 having convex ribs is about 102 Newtons. In an embodiment, the expandable body 770 having convex ribs provides additional contact area between the expandable body 770 and the fracture site and allows the expandable body 770 to compress and conform to the irregular surface of a fracture.

FIG. 9A, FIG. 9B and FIG. 9C are close-up views of an embodiment of an expandable body of the present disclosure which can be part of the system 100 of FIG. 1. The expandable body 870 is shown in an expanded state. The expandable body 870 includes a closed end 873, a sealable open end 875, an inner cavity (not visible), an external surface 874 and an internal surface (not visible). The fluid that can be infused into the inner cavity of the expandable body 870 includes, but is not limited to, air and light-sensitive liquid 165. Expandable body 870 has an insertion depth with a fixed dimension, a width with a fixed dimension, and a thickness with a changeable dimension to provide appropriate distraction to a bone, wherein entry of a fluid into the inner cavity of the expandable body 870 changes the dimension of the expandable body 870 thickness or distraction that the hardened expandable body 870 provides. The insertion depth and the width are fixed dimensions, and are not affected by the infusion of fluid into the expandable body 870. Modification of light-sensitive liquid 165 infusion allows a user to adjust the span or thickness of the expandable body 870 to customize the angulation and distraction of the expandable body 870 to provide a user-specific size and shape for the animal. In that the expandable body 7870 is formable and shapeable by the surgeon prior to the photocuring of the light-sensitive liquid 165 in the expandable body 870, the resultant implant best mirrors the size and shape of the area that the implant is stabilizing, and that the shape attempts to maximize the surface contact area, minimizing specific points of concentrated pressure. In an embodiment, the expandable body 870 design provides excellent compressive strength, thus minimizing deformation under dynamic loading conditions. The implant has a compressive modulus that is close to that of cancellous bone, allowing the natural transfer of dynamic loads away from the implant to the surrounding bone.

In an embodiment, the external surface 874 of the expandable body 870 is resilient and puncture resistant. In an embodiment, the expandable body 870 is manufactured from a non-compliant (non-stretch/non-expansion) conformable material including but not limited to urethane, polyethylene terephthalate (PET), nylon elastomer and other similar polymers. In an embodiment, the expandable body 870 is manufactured from a polyethylene terephthalate (PET).

As illustrated in FIG. 9A, FIG. 9B and FIG. 9C, at least a portion of the external surface 874 of the expandable body 870 is substantially even and smooth and at least a portion of the external surface 874 of the expandable body 870 includes a plurality of textured elements 877 or concave ribs that completely surround the external surface 874. In an embodiment, the expandable body 870 includes one, two, three, four, five, six, seven, eight, nine, ten or more than ten concave ribs. In an embodiment, each concave rib may be between about 2 mm and about 5 mm in width. In an embodiment, the concave ribs may each be substantially the same width. In an embodiment, the concave ribs may be of varying width. In an embodiment, the plurality of textured elements 877 improves the grip and stability of the expandable body 870 after the expandable body 870 is inserted into the fracture or osteotomy location. The expandable body 870 is thicker at a proximal area 876 (the area engaging the delivery catheter 150) and tapers in thickness as it approaches a distal area 878. A distal area 878 that tapers may allow for easier insertion of the expandable body 870. In an embodiment, the pullout strength for the hardened expandable body 870 having concave ribs is between approximately 40 Newtons and about 100 Newtons. In an embodiment, the pullout strength for the hardened expandable body 870 having concave ribs is about 63 Newtons.

Figures 10A, 10B, 10C:
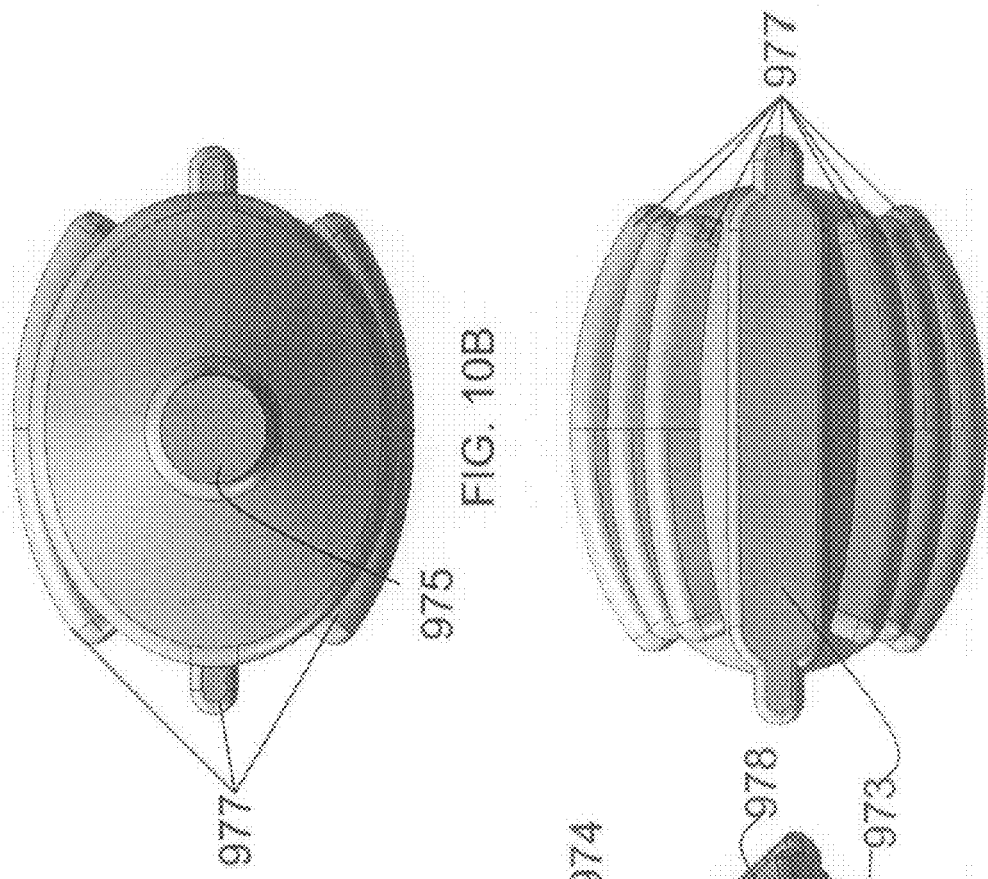
FIG. 10A, FIG. 10B and FIG. 10C are close-up views of an embodiment of an expandable body of the present disclosure which can be part of the system of FIG. 1. The expandable body is shown in an expanded state.

FIG. 10A, FIG. 10B and FIG. 10C are close-up views of an embodiment of an expandable body 970 of the present disclosure which can be part of the system 100 of FIG. 1. The expandable body 970 is shown in an expanded state. The expandable body 970 includes a closed end 973, a sealable open end 975, an inner cavity (not visible), an external surface 974 and an internal surface (not visible). The fluid that can be infused into the inner cavity of the expandable body 970 includes, but is not limited to, air and light-sensitive liquid 165. Expandable body 970 has an insertion depth with a fixed dimension, a width with a fixed dimension, and a thickness with a changeable dimension to provide appropriate distraction to a bone, wherein entry of a fluid into the inner cavity of the expandable body 970 changes the dimension of the expandable body 970 thickness or distraction that the hardened expandable body 970 provides. The insertion depth and the width are fixed dimensions, and are not affected by the infusion of fluid into the expandable body 970. Modification of light-sensitive liquid 165 infusion allows a user to adjust the span or thickness of the expandable body 970 to customize the angulation and distraction of the expandable body 970 to provide a user-specific size and shape for the animal. In that the expandable body 970 is formable and shapeable by the surgeon prior to the photocuring of the light-sensitive liquid 165 in the expandable body 970, the resultant implant best mirrors the size and shape of the area that the implant is stabilizing, and that the shape attempts to maximize the surface contact area, minimizing specific points of concentrated pressure. In an embodiment, the expandable body 970 design provides excellent compressive strength, thus minimizing deformation under dynamic loading conditions. The implant has a compressive modulus that is close to that of cancellous bone, allowing the natural transfer of dynamic loads away from the implant to the surrounding bone.

In an embodiment, the external surface 974 of the expandable body 970 is resilient and puncture resistant. In an embodiment, the expandable body 970 is manufactured from a non-compliant (non-stretch/non-expansion) conformable material including but not limited to urethane, polyethylene terephthalate (PET), nylon elastomer and other similar polymers. In an embodiment, the expandable body 970 is manufactured from a polyethylene terephthalate (PET).

As illustrated in FIG. 10A, FIG. 10B and FIG. 10C, at least a portion of the external surface 974 of the expandable body 970 is substantially even and smooth and at least a portion of the external surface 974 of the expandable body 970 includes a plurality of textured elements 977 or bumps. In an embodiment, the plurality of textured elements 977 improves the grip and stability of the expandable body 970 after the expandable body 970 is inserted into the fracture or osteotomy location. The plurality of textured elements 977 are positioned on a top face, a bottom face, and the side faces of the external surface 974. The plurality of textured elements 977 are not contiguous or circumferential, ensuring that the expansion/filling of the expandable body 970 causes the expandable body 970 to expand in diameter, rather than to expand in length. The expandable body 970 is thicker at a proximal area 976 (the area engaging the delivery catheter 150) and tapers in thickness as it approaches a distal area 978. A distal area 978 that tapers may allow for easier insertion of the expandable body 970.

FIGS. 11A-11H show an embodiment of steps performed during a method of treatment of a fractured bone 1100 using the system 100 of the present disclosure. As described above, system 100 includes an expandable body 170 of the present disclosure sufficiently designed to be infused with a photodynamic (light curable) material, and exposed to an appropriate frequency of light and intensity to cure the material inside the expandable body 170 and form a photodynamic device 1150. In an embodiment, a photodynamic device of the present disclosure is used to re-align a fractured bone. In an embodiment, a photodynamic device of the present disclosure is used to stabilize a fractured bone. In an embodiment, a photodynamic device of the present disclosure is capable of providing the appropriate angulation and distraction to a fractured bone to provide specific implant size and shape for an animal. In an embodiment, a photodynamic device of the present disclosure provides support, stability and distraction of the identified bone surfaces during the natural healing process of the bone. An expandable body 170 of the present disclosure, and associated components, are typically provided sterile. An expandable body 170 of the present disclosure is recommended for single use.

Figure 11A:
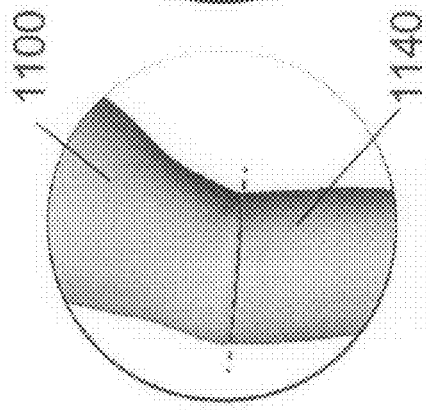
FIGS. 11A-11H show an embodiment of method steps for the alignment, distraction and stabilization of a fractured distal radius.
Figure 11B:
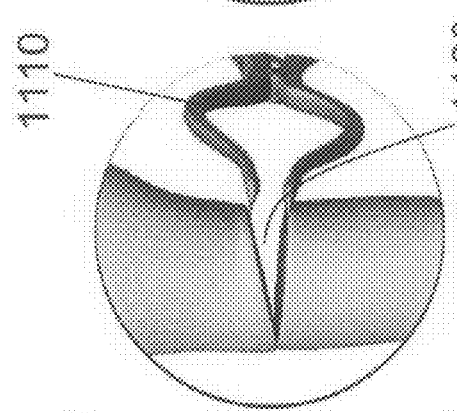
Figure 11C:
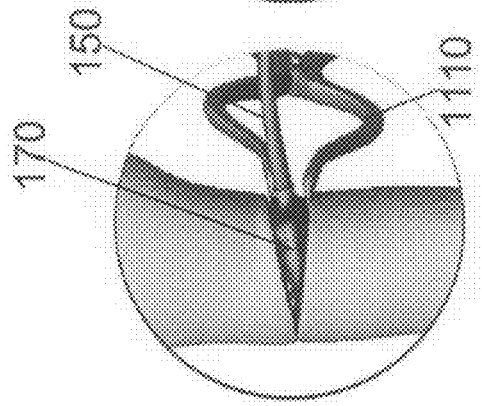
Figure 11D:
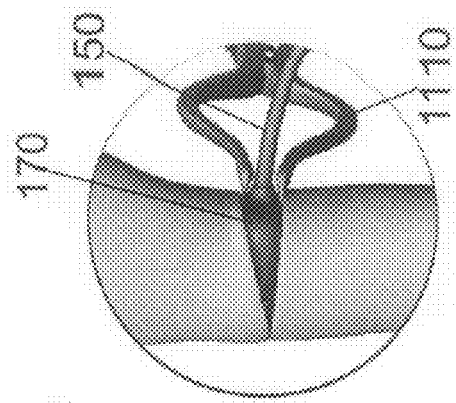
Figure 11E:
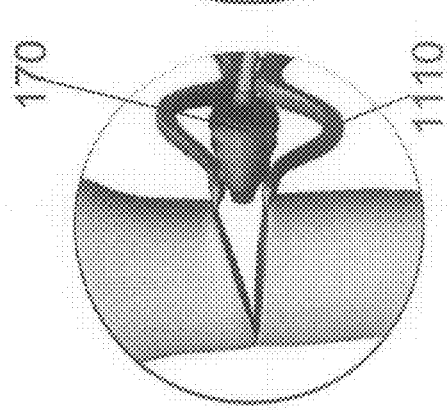
Figure 11F:
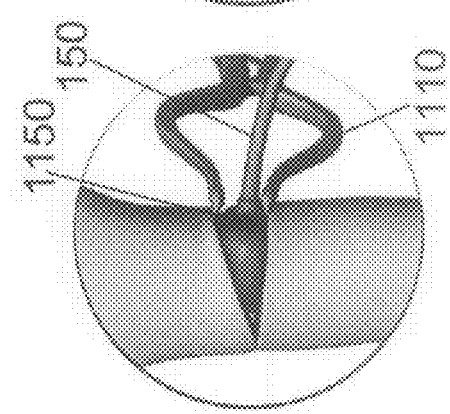
Figure 11G:
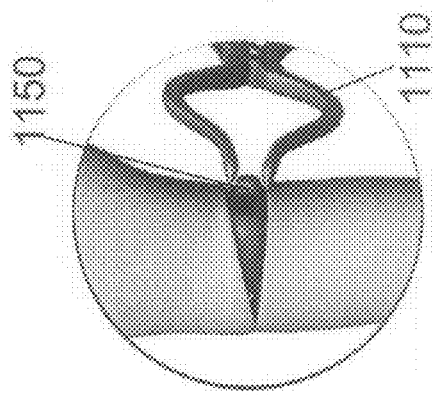
Figure 11H:
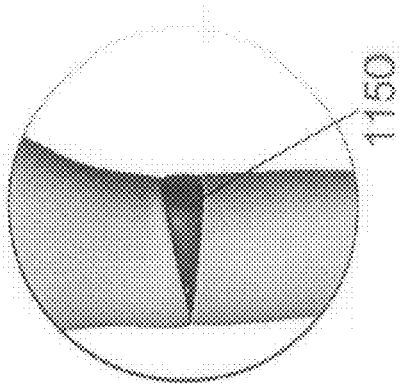

In an embodiment, traction may be applied to the injured limb before surgery. Alternatively, conventional bone distraction instrumentation can be utilized or the use of K wires delivered to the lateral aspect of the bone (proximal and distal to the fracture) to assist in the initial manipulation and distraction/reduction of the bones. As illustrated in FIG. 11A, access to a bone is achieved. In an embodiment, a minimally invasive incision is made in the skin of the animal to expose the site and the tendons, muscles and/or nerves are carefully retracted. In the case where an osteotomy is required—an appropriate sized (~10 mm to about 15 mm) osteotomy is made using standard procedures, and the cut is finished with, for example, an osteotome. Anatomical correction can be performed by initially distracting the osteotomy site through either traction or surgical instrumentation, to provide, for example an initial distraction between about 8 mm and about 12 mm. As illustrated in FIG. 11B, in an embodiment a distraction instrument 1110 is installed to provide controlled initial distraction of the bones 1100/1140 and to maintain a span 1120 during the fitting of the expandable body 170. If pin distraction is utilized—with the aide of K wires—the K wires can be placed on either side of the osteotomy. Alternatively conventional wedge shaped distraction and measurement instrumentation can also be used to achieve the initial distraction. The instrumentation is engaged between the bone 1100/1140 surfaces and advanced until the correct amount of initial distraction is achieved. Once the correct amount of initial distraction has been achieved—as confirmed by fluoroscopy, and measurements of the span 1120 have been taken towards the determination of the correct device size, the expandable body 170 is delivered to the surgical site for trial sizing, as illustrated in FIG. 11C. In an embodiment, the expandable body 170 is percutaneously delivered to the surgical site. In an embodiment, the expandable body 170 is delivered to the surgical site so that the expandable body 170 is inserted approximately 90° to the orientation of the radius shaft length. In an embodiment, sizing of the expandable body 170 towards the correct distraction size is accomplished by filling the expandable body 170 with air through the use of a standard syringe, as illustrated in FIG. 11D. With the use of fluoroscopy, and distraction provided and maintained through ancillary instrumentation, the uninflated expandable body 170 is inserted between the bone 1100/1140 surfaces of the span 1120. In an embodiment, the expandable body 170 is manufactured from a radiolucent material which permit x-rays to pass through the expandable body 170 so that the entire body 170 can be viewed during the procedure. Once in position, and while the initial distraction is maintained by ancillary instrumentation or external fraction, the expandable body 170 is inflated with air until the thickness or distraction of the expandable body 170 matches the size of the osteotomy. In general, the air-filled syringe is attached to a port at the proximal end of the delivery catheter 150, and the syringe aspirated so that the air travels through the inner void 152 or the inner lumen 154 to fill and inflate the expandable body 170. The expandable body 170 is inflated so that the body 170 is securely nested within the span 1120 of the bone 1100/1140 surfaces to provide an optimal stable environment for bone remodeling, thus the correct footprint and thickness of the expandable body 170 is determined. The volume of air within the syringe is determined, as this will be the same amount of light-sensitive liquid 165 to infuse within the system 100 to achieve the similar size expandable body 170. All of the air is evacuated out of the expandable body 170. A sterile vial of light-sensitive liquid 165 is opened and the monomer withdrawn into a syringe. A luer fitting on the system 100 is filled with a small amount of light-sensitive liquid 165, and then the light-sensitive liquid infusion syringe is attached to the luer fitting. The same volume of light-sensitive liquid 165 (determined at sizing with air) should be infused within the system 100. In an embodiment, the light-sensitive liquid 165 is a radiolucent liquid which permits x-rays to pass through the light-sensitive liquid 165 so that the expandable body 170 can be viewed during inflation. The light source 110/light pipe 120 is connected to the system 100, and the light-conducting fiber 140 is delivered through the inner lumen 154 of the delivery catheter 150 towards the expandable body 170. The appropriate volume of light-sensitive liquid 165 is infused into the inner void 152 of the delivery catheter 150 into the expandable body 170. The expandable body 170 is cured by activating the light source 110 to communicate light energy to the light-conducting fiber 140. After the light-sensitive liquid 165 has been hardened within the expandable body 170 the light-conducting fiber 140 can be removed from the delivery catheter 150. In an embodiment, as illustrated in FIG. 11E, once the correct footprint and thickness of the expandable body 170 is determined, the expandable body 170 may be removed from the surgical site within the animal and the above steps carried out on a sterile preparation table or other appropriate sterile site. In other embodiments, once the correct footprint and thickness of the expandable body 170 is determined, the above steps are carried out in situ without the need to remove the expandable body 170 from the surgical site. FIG. 11F shows the re-implantation of the cured expandable body 170 if the expandable body 170 was removed from the surgical site to be cured. The expandable body 170 once hardened, may be released from the delivery catheter 150, as illustrated in FIG. 11G, and forms a photodynamic device 1150 of the present disclosure. In an embodiment, the photodynamic device 1150 resides completely in the cancellous bone and does not protrude beyond the surfaces of the bone, as illustrated in FIG. 11H. In an embodiment, each surface of the photodynamic device 1150 may be in contact with the bone 1100/1140 surfaces as a means to cause reduction. In an embodiment, at least a portion of a surface of the photodynamic device 1150 may be in contact with the bone 1100/1140 surfaces as a means to cause reduction. The photodynamic device 1150 provides distraction of the bone 1100/1140 fragments to re-align the bone 1100/1140. In an embodiment, the photodynamic device 1150 provides appropriate distraction to re-align, stabilize and restore angulation to the bone, without the aid of screws, fasteners, plates, rods or any other similar ancillary distraction device. In an embodiment, the photodynamic device 1150 provides appropriate distraction to re-align, stabilize and restore angulation to the bone, without the aid of screws, fasteners, plates, rods or any other similar ancillary distraction device engaged into the proximal and distal segment of the fractured bone. The photodynamic device 1150 can provide contact-compression at the bone 1100/1140 surfaces. In the embodiment where the expandable body 170 is manufactured from a radiolucent material, the photodynamic device 1150 can be monitored post operatively by the use of x rays or other imaging systems, and the healing of the fracture site can be visualized without interference.

Figure 13:
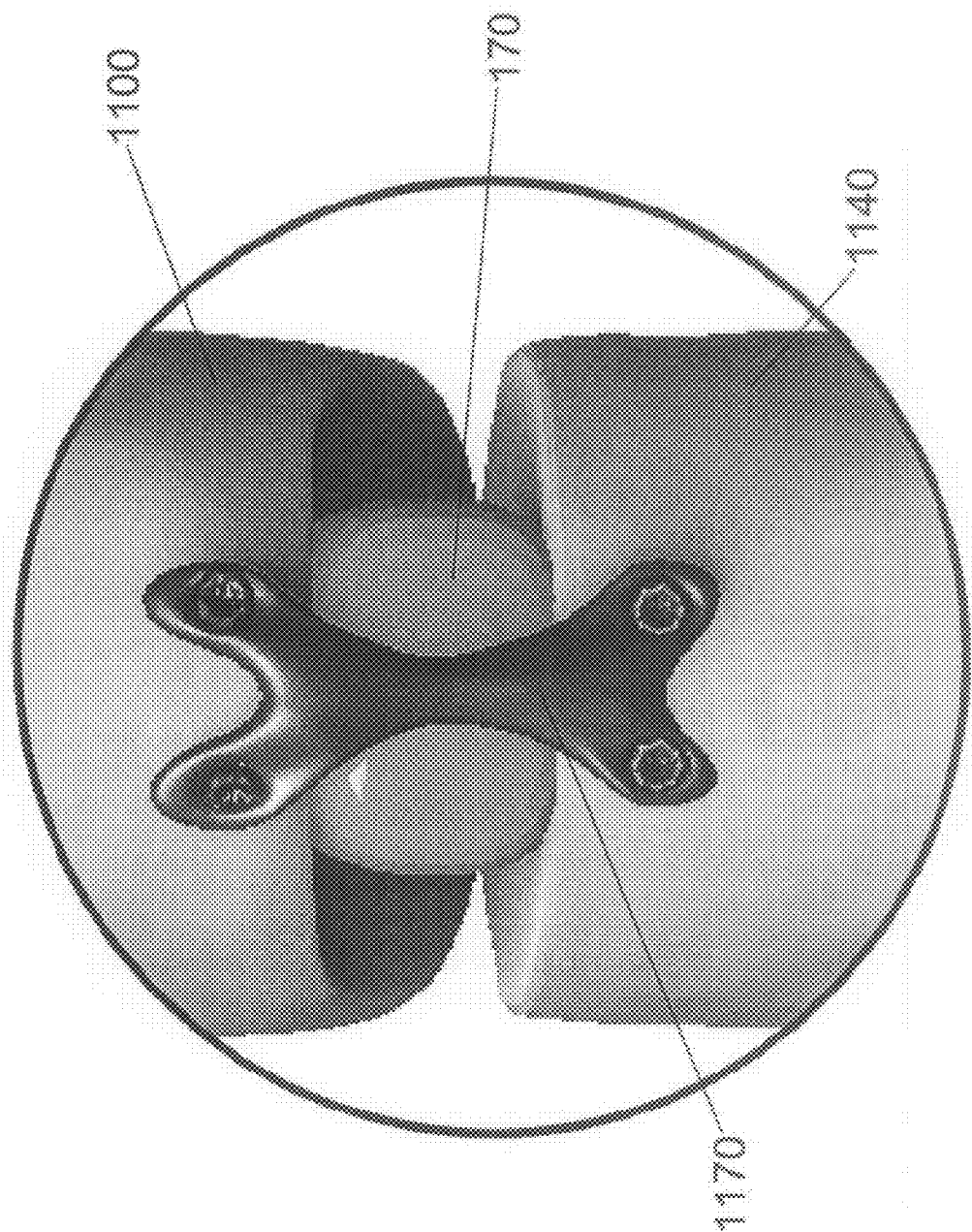
FIG. 13 shows a close-up view of an embodiment of a photodynamic device of the present disclosure with ancillary fixation.

Use of ancillary fixation is optional for improving stability. As illustrated in FIG. 12, in an embodiment the ancillary fixation are K wires 12160 that abut the photodynamic device 1150 and improve stability. As illustrated in FIG. 13, in an embodiment the ancillary fixation is a surface plate 1170 and improve stability. In an embodiment, the ancillary fixation can be positioned through the photodynamic device 1150 to improve stability.

In an embodiment, a photodynamic device of the present disclosure can be used in the angular correction of bones in the hand and wrist, the forearm, and the foot and ankle of an animal. In an embodiment, the initial angular correction can be reduced in conventional fashion through the use of external mechanical manipulation, traction or through the use of standard surgical instruments designed to assist in bone distraction. Once the required amount of distraction and angulation has been satisfactorily achieved via conventional means, an implant size is determined by placing an empty, unfilled expandable body of the present disclosure within the created space, and filling the expandable body with air to create a stable interface between the surfaces of the bone and the expandable body. Fluroscopy may be utilized to assist in the determination of the correct amount of distraction, and to assess the positioning of the expandable body. The required amount of air volume to achieve the specific inflation of the expandable body edge is measured on the syringe, which determines the required volume of monomer to be infused into the expandable body. The air is then evacuated from the expandable body, and the expandable body is filled with the photodynamic light-sensitive liquid monomer. In an embodiment, the expandable body is filled with the determined amount of photodynamic light-sensitive liquid monomer and cured in situ. Once the expandable body has been illuminated and cured, the cured and hardened device is then reinserted and placed within the gap in the bone. In an embodiment, the expandable body is filled with the determined amount of photodynamic light-sensitive liquid monomer and cured on a sterile preparation table or other appropriate sterile site. In an embodiment, placement of the hardened device within the gap in the bone re-aligns the bone. In an embodiment, placement of the hardened device within the gap in the bone stabilizes the bone. In an embodiment, placement of the hardened device within the gap in the bone maintains distraction of the bone. In an embodiment, placement of the hardened device within the gap in the bone restores proper angulation of the bone. The design of the implant allows the implant to accommodate a variety of bone applications. The use of the infusable implant shape allows a surgeon the ability to modify the distraction thickness of the expandable body, the thickness of the expandable body can be adjusted through the infusion of either more or less light-sensitive liquid monomer to achieve the appropriate thickness or distraction of the expandable body, while none of the other dimensions are affected. In an embodiment, a photodynamic device of the present disclosure provides support, stability, angulation and maintains distraction of the identified bone surfaces during the natural healing process of the bone. The expandable body has a shape to substantially fill the interior space of a bone fracture.

A method of maintaining distraction of a fractured distal radius bone includes providing temporary distraction to a fractured distal radius bone to provide a distraction gap; delivering an expandable body in an unexpanded state into the distraction gap; infusing a first fluid into the expandable body to expand the expandable body so that a desired amount of distraction is achieved at the distraction gap; removing the first fluid from the expandable body; determining an amount of first fluid removed from the expandable body; infusing an amount of light-sensitive liquid into the expandable body to expand the expandable body, wherein the amount of light-sensitive liquid is substantially equivalent to the amount of first fluid; curing the light-sensitive liquid in the expandable body to form a rigid photodynamic device; and maintaining a desired amount of distraction at the distraction gap.

A method of maintaining distraction of a fractured distal radius bone includes providing temporary distraction to a fractured distal radius bone to provide a distraction gap; delivering an expandable body in an unexpanded state into the distraction gap; infusing a first fluid into the expandable body to expand the expandable body so that a desired amount of distraction is achieved at the distraction gap; removing the first fluid from the expandable body; removing the expanded expandable body from the distraction gap; determining an amount of first fluid removed from the expandable body; infusing an amount of light-sensitive liquid into the expandable body to expand the expandable body, wherein the amount of light-sensitive liquid is substantially equivalent to the amount of first fluid; curing the light-sensitive liquid in the expandable body to form a rigid photodynamic device; and implanting the photodynamic device into the distraction gap to maintain the desired amount of distraction at the distraction gap.

All patents, patent applications, and published references cited herein are hereby incorporated by reference in their entirety. It will be appreciated that several of the above-disclosed and other features and functions, or alternatives thereof, may be desirably combined into many other different systems or application. Various presently unforeseen or unanticipated alternatives, modifications, variations, or improvements therein may be subsequently made by those skilled in the art.

What is claimed is:

1. A method of maintaining distraction of a bone comprising:
   providing temporary distraction to a fractured distal radius bone to provide a distraction gap;
   delivering an expandable body in an unexpanded state into the distraction gap, the expandable body having an insertion depth with a fixed dimension, a width with a fixed dimension, and a the distraction thickness with a the changeable dimension wherein the insertion depth is a length between a sealable end and a closed end of the expandable body;
   infusing a first fluid into the expandable body to expand the expandable body so that a desired amount of distraction is achieved at the distraction gap;
   removing the first fluid from the expandable body;

determining an amount of the first fluid removed from the expandable body;

infusing an amount of a light-sensitive liquid through the open end into an open inner cavity of the expandable body that adjustably changes the distraction thickness of the expandable body without changing the insertion depth or width of the expandable body, wherein the amount of light-sensitive liquid is substantially equivalent to the amount of the first fluid;

curing the light-sensitive liquid in the expandable body to form a rigid photodynamic device; and maintaining a desired amount of distraction at the distraction gap.

2. The method of claim 1, further comprising distracting the distal radius bone so that a radial length of the distal radius bone is returned to a normal range of about 12 mm.

3. The method of claim 1, further comprising distracting the distal radius bone so that a palmar tilt of the distal radius bone is returned to a normal range of about 11°.

4. The method of claim 1, further comprising changing the changeable dimension of the distraction thickness of the expandable body by adding or removing the light sensitive liquid, without changing the dimension of the insertion depth and the dimension of the width of the expandable body.

5. The method of claim 1, wherein the insertion depth is a length between the sealable open end and the closed end of the expandable body.

6. A method of maintaining distraction of a fractured distal radius bone comprising:

providing temporary distraction to a fractured distal radius bone to provide a distraction gap;

delivering an expandable body in an unexpanded state into the distraction gap, the expandable body removably attached to a distal end of a delivery catheter, wherein the expandable body has a closed end, a sealable open end, an inner cavity for passage of the light-sensitive liquid, and wherein the expandable body has an insertion depth with a fixed dimension, a width with a fixed dimension, and a distraction thickness with a changeable dimension, wherein the insertion depth is a length between the sealable end and the closed end of the expandable body;

infusing an amount of a light-sensitive liquid through the open end into the inner cavity of the expandable body that adjustably changes the distraction thickness of the expandable body without changing the insertion depth or the width of the expandable body;

curing the light-sensitive liquid in the inner cavity of the expandable body;

removing the expandable body from the delivery catheter to form a rigid photodynamic device.

7. The method of claim 6 wherein the expandable body has an insertion depth with a fixed dimension, a width with a fixed dimension.

8. The method of claim 6 wherein implanting the photodynamic device into the distraction gap distracts the distal radius bone so that a radial length of the distal radius bone is returned to a normal range of about 12 mm.

9. The method of claim 6 wherein implanting the photodynamic device into the distraction gap distracts the distal radius bone so that a palmar tilt of the distal radius bone is returned to a normal range of about 11°.

* * * * *